(12) United States Patent
Kostrzewski et al.

(10) Patent No.: US 10,939,968 B2
(45) Date of Patent: Mar. 9, 2021

(54) STERILE HANDLE FOR CONTROLLING A ROBOTIC SURGICAL SYSTEM FROM A STERILE FIELD

(71) Applicant: KB MEDICAL, SA, Audubon, PA (US)

(72) Inventors: Szymon Kostrzewski, Lausanne (CH); Billy Nussbaumer, Preverenges (CH)

(73) Assignee: Globus Medical Inc., Audubon, PA (US)

( * ) Notice: Subject to any disclaimer, the term of this patent is extended or adjusted under 35 U.S.C. 154(b) by 168 days.

(21) Appl. No.: 16/026,272

(22) Filed: Jul. 3, 2018

(65) Prior Publication Data

US 2018/0325609 A1 Nov. 15, 2018

Related U.S. Application Data

(63) Continuation of application No. 14/619,732, filed on Feb. 11, 2015, now Pat. No. 10,039,605.

(Continued)

(51) Int. Cl.
*A61B 34/00* (2016.01)
*A61B 34/30* (2016.01)
*A61B 17/16* (2006.01)
*A61B 17/17* (2006.01)
*A61B 46/10* (2016.01)
(Continued)

(52) U.S. Cl.
CPC .......... *A61B 34/30* (2016.02); *A61B 17/1615* (2013.01); *A61B 17/1655* (2013.01); *A61B 17/17* (2013.01); *A61B 34/70* (2016.02); *A61B 34/74* (2016.02); *A61B 46/10* (2016.02); *A61B 90/40* (2016.02); *A61B 2017/00022* (2013.01); *A61B 2017/0023* (2013.01); *A61B 2017/0042* (2013.01); *A61B 2017/0046* (2013.01); *A61B 2017/00371* (2013.01); *A61B 2017/00384* (2013.01); *A61B 2017/00477* (2013.01);
(Continued)

(58) Field of Classification Search
CPC ......... A61B 34/30; A61B 34/70; A61B 34/74; A61B 2034/301–303; A61B 17/17
See application file for complete search history.

(56) References Cited

U.S. PATENT DOCUMENTS

| 4,150,293 A | 4/1979 | Franke |
| 5,246,010 A | 9/1993 | Gazzara et al. |

(Continued)

OTHER PUBLICATIONS

US 8,231,638 B2, 07/2012, Swarup et al. (withdrawn)

*Primary Examiner* — Eric D. Bertram

(57) ABSTRACT

An implant for therapeutically separating bones of a joint has two endplates each having an opening through the endplate, and at least one ramped surface on a side opposite a bone engaging side. A frame is slideably connected to the endplates to enable the endplates to move relative to each other at an angle with respect to the longitudinal axis of the implant, in sliding connection with the frame. An actuator screw is rotatably connected to the frame. A carriage forms an open area aligned with the openings in the endplates. The openings in the endplates pass through the carriage to form an unimpeded passage from bone to bone of the joint. The carriage has ramps which mate with the ramped surfaces of the endplates, wherein when the carriage is moved by rotation of the actuator screw, the endplates move closer or farther apart.

20 Claims, 21 Drawing Sheets

Related U.S. Application Data

(60) Provisional application No. 61/950,550, filed on Mar. 10, 2014, provisional application No. 61/938,423, filed on Feb. 11, 2014.

(51) Int. Cl.
*A61B 90/40* (2016.01)
*A61B 17/00* (2006.01)
*A61B 34/20* (2016.01)
*A61B 90/00* (2016.01)

(52) U.S. Cl.
CPC ............... *A61B 2034/2055* (2016.02); *A61B 2090/0813* (2016.02)

(56) References Cited

U.S. PATENT DOCUMENTS

| | | |
|---|---|---|
| 5,354,314 A | 10/1994 | Hardy et al. |
| 5,397,323 A | 3/1995 | Taylor et al. |
| 5,598,453 A | 1/1997 | Baba et al. |
| 5,772,594 A | 6/1998 | Barrick |
| 5,791,908 A | 8/1998 | Gillio |
| 5,820,559 A | 10/1998 | Ng et al. |
| 5,825,982 A | 10/1998 | Wright et al. |
| 5,887,121 A | 3/1999 | Funda et al. |
| 5,911,449 A | 6/1999 | Daniele et al. |
| 5,951,475 A | 9/1999 | Gueziec et al. |
| 5,987,960 A | 11/1999 | Messner et al. |
| 6,012,216 A | 1/2000 | Esteves et al. |
| 6,031,888 A | 2/2000 | Ivan et al. |
| 6,033,415 A | 3/2000 | Mittelstadt et al. |
| 6,080,181 A | 6/2000 | Jensen et al. |
| 6,106,511 A | 8/2000 | Jensen |
| 6,122,541 A | 9/2000 | Cosman et al. |
| 6,144,875 A | 11/2000 | Schweikard et al. |
| 6,157,853 A | 12/2000 | Blume et al. |
| 6,167,145 A | 12/2000 | Foley et al. |
| 6,167,292 A | 12/2000 | Badano et al. |
| 6,201,984 B1 | 3/2001 | Funda et al. |
| 6,203,196 B1 | 3/2001 | Meyer et al. |
| 6,205,411 B1 | 3/2001 | DiGioia, III et al. |
| 6,212,419 B1 | 4/2001 | Blume et al. |
| 6,231,565 B1 | 5/2001 | Tovey et al. |
| 6,236,875 B1 | 5/2001 | Bucholz et al. |
| 6,246,900 B1 | 6/2001 | Cosman et al. |
| 6,301,495 B1 | 10/2001 | Gueziec et al. |
| 6,306,126 B1 | 10/2001 | Montezuma |
| 6,312,435 B1 | 11/2001 | Wallace et al. |
| 6,314,311 B1 | 11/2001 | Williams et al. |
| 6,320,929 B1 | 11/2001 | Von Der Haar |
| 6,322,567 B1 | 11/2001 | Mittelstadt et al. |
| 6,325,808 B1 | 12/2001 | Bernard et al. |
| 6,340,363 B1 | 1/2002 | Bolger et al. |
| 6,377,011 B1 | 4/2002 | Ben-Ur |
| 6,379,302 B1 | 4/2002 | Kessman et al. |
| 6,402,762 B2 | 6/2002 | Hunter et al. |
| 6,424,885 B1 | 7/2002 | Niemeyer et al. |
| 6,447,503 B1 | 9/2002 | Wynne et al. |
| 6,451,027 B1 | 9/2002 | Cooper et al. |
| 6,477,400 B1 | 11/2002 | Barrick |
| 6,484,049 B1 | 11/2002 | Seeley et al. |
| 6,487,267 B1 | 11/2002 | Wolter |
| 6,490,467 B1 | 12/2002 | Bucholz et al. |
| 6,490,475 B1 | 12/2002 | Seeley et al. |
| 6,499,488 B1 | 12/2002 | Hunter et al. |
| 6,501,981 B1 | 12/2002 | Schweikard et al. |
| 6,507,751 B2 | 1/2003 | Blume et al. |
| 6,535,756 B1 | 3/2003 | Simon et al. |
| 6,560,354 B1 | 5/2003 | Maurer, Jr. et al. |
| 6,565,554 B1 | 5/2003 | Niemeyer |
| 6,587,750 B2 | 7/2003 | Gerbi et al. |
| 6,614,453 B1 | 9/2003 | Sun et al. |
| 6,614,871 B1 | 9/2003 | Kobiki et al. |
| 6,619,840 B2 | 9/2003 | Rasche et al. |
| 6,636,757 B1 | 10/2003 | Jascob et al. |
| 6,645,196 B1 | 11/2003 | Nixon et al. |
| 6,666,579 B2 | 12/2003 | Jensen |
| 6,669,635 B2 | 12/2003 | Kessman et al. |
| 6,701,173 B2 | 3/2004 | Nowinski et al. |
| 6,757,068 B2 | 6/2004 | Foxlin |
| 6,782,287 B2 | 8/2004 | Grzeszczuk et al. |
| 6,783,524 B2 | 8/2004 | Anderson et al. |
| 6,786,896 B1 | 9/2004 | Madhani et al. |
| 6,788,018 B1 | 9/2004 | Blumenkranz |
| 6,804,581 B2 | 10/2004 | Wang et al. |
| 6,823,207 B1 | 11/2004 | Jensen et al. |
| 6,827,351 B2 | 12/2004 | Graziani et al. |
| 6,837,892 B2 | 1/2005 | Shoham |
| 6,839,612 B2 | 1/2005 | Sanchez et al. |
| 6,856,826 B2 | 2/2005 | Seeley et al. |
| 6,856,827 B2 | 2/2005 | Seeley et al. |
| 6,879,880 B2 | 4/2005 | Nowlin et al. |
| 6,892,090 B2 | 5/2005 | Verard et al. |
| 6,920,347 B2 | 7/2005 | Simon et al. |
| 6,922,632 B2 | 7/2005 | Foxlin |
| 6,968,224 B2 | 11/2005 | Kessman et al. |
| 6,978,166 B2 | 12/2005 | Foley et al. |
| 6,988,009 B2 | 1/2006 | Grimm et al. |
| 6,991,627 B2 | 1/2006 | Madhani et al. |
| 6,996,487 B2 | 2/2006 | Jutras et al. |
| 6,999,852 B2 | 2/2006 | Green |
| 7,007,699 B2 | 3/2006 | Martinelli et al. |
| 7,016,457 B1 | 3/2006 | Senzig et al. |
| 7,043,961 B2 | 5/2006 | Pandey et al. |
| 7,062,006 B1 | 6/2006 | Pelc et al. |
| 7,063,705 B2 | 6/2006 | Young et al. |
| 7,072,707 B2 | 7/2006 | Galloway, Jr. et al. |
| 7,083,615 B2 | 8/2006 | Peterson et al. |
| 7,097,640 B2 | 8/2006 | Wang et al. |
| 7,099,428 B2 | 8/2006 | Clinthorne et al. |
| 7,108,421 B2 | 9/2006 | Gregerson et al. |
| 7,130,676 B2 | 10/2006 | Barrick |
| 7,139,418 B2 | 11/2006 | Abovitz et al. |
| 7,139,601 B2 | 11/2006 | Bucholz et al. |
| 7,155,316 B2 | 12/2006 | Sutherland et al. |
| 7,164,968 B2 | 1/2007 | Treat et al. |
| 7,167,738 B2 | 1/2007 | Schweikard et al. |
| 7,169,141 B2 | 1/2007 | Brock et al. |
| 7,172,627 B2 | 2/2007 | Fiere et al. |
| 7,194,120 B2 | 3/2007 | Wicker et al. |
| 7,197,107 B2 | 3/2007 | Arai et al. |
| 7,231,014 B2 | 6/2007 | Levy |
| 7,231,063 B2 | 6/2007 | Naimark et al. |
| 7,239,940 B2 | 7/2007 | Wang et al. |
| 7,248,914 B2 | 7/2007 | Hastings et al. |
| 7,301,648 B2 | 11/2007 | Foxlin |
| 7,302,288 B1 | 11/2007 | Schellenberg |
| 7,313,430 B2 | 12/2007 | Urquhart et al. |
| 7,318,805 B2 | 1/2008 | Schweikard et al. |
| 7,318,827 B2 | 1/2008 | Leitner et al. |
| 7,319,897 B2 | 1/2008 | Leitner et al. |
| 7,324,623 B2 | 1/2008 | Heuscher et al. |
| 7,327,865 B2 | 2/2008 | Fu et al. |
| 7,331,967 B2 | 2/2008 | Lee et al. |
| 7,333,642 B2 | 2/2008 | Green |
| 7,339,341 B2 | 3/2008 | Oleynikov et al. |
| 7,366,562 B2 | 4/2008 | Dukesherer et al. |
| 7,379,790 B2 | 5/2008 | Toth et al. |
| 7,386,365 B2 | 6/2008 | Nixon |
| 7,422,592 B2 | 9/2008 | Morley et al. |
| 7,435,216 B2 | 10/2008 | Kwon et al. |
| 7,440,793 B2 | 10/2008 | Chauhan et al. |
| 7,460,637 B2 | 12/2008 | Clinthorne et al. |
| 7,466,303 B2 | 12/2008 | Yi et al. |
| 7,493,153 B2 | 2/2009 | Ahmed et al. |
| 7,505,617 B2 | 3/2009 | Fu et al. |
| 7,533,892 B2 | 5/2009 | Schena et al. |
| 7,542,791 B2 | 6/2009 | Mire et al. |
| 7,555,331 B2 | 6/2009 | Viswanathan |
| 7,567,834 B2 | 7/2009 | Clayton et al. |
| 7,594,912 B2 | 9/2009 | Cooper et al. |
| 7,606,613 B2 | 10/2009 | Simon et al. |
| 7,607,440 B2 | 10/2009 | Coste-Maniere et al. |

(56) References Cited

U.S. PATENT DOCUMENTS

| | | |
|---|---|---|
| 7,623,902 B2 | 11/2009 | Pacheco |
| 7,630,752 B2 | 12/2009 | Viswanathan |
| 7,630,753 B2 | 12/2009 | Simon et al. |
| 7,643,862 B2 | 1/2010 | Schoenefeld |
| 7,660,623 B2 | 2/2010 | Hunter et al. |
| 7,661,881 B2 | 2/2010 | Gregerson et al. |
| 7,683,331 B2 | 3/2010 | Chang |
| 7,683,332 B2 | 3/2010 | Chang |
| 7,689,320 B2 | 3/2010 | Prisco et al. |
| 7,691,098 B2 | 4/2010 | Wallace et al. |
| 7,702,379 B2 | 4/2010 | Avinash et al. |
| 7,702,477 B2 | 4/2010 | Tuemmler et al. |
| 7,711,083 B2 | 5/2010 | Heigl et al. |
| 7,711,406 B2 | 5/2010 | Kuhn et al. |
| 7,720,523 B2 | 5/2010 | Omernick et al. |
| 7,725,253 B2 | 5/2010 | Foxlin |
| 7,726,171 B2 | 6/2010 | Langlotz et al. |
| 7,742,801 B2 | 6/2010 | Neubauer et al. |
| 7,751,865 B2 | 7/2010 | Jascob et al. |
| 7,760,849 B2 | 7/2010 | Zhang |
| 7,762,825 B2 | 7/2010 | Burbank et al. |
| 7,763,015 B2 | 7/2010 | Cooper et al. |
| 7,787,699 B2 | 8/2010 | Mahesh et al. |
| 7,796,728 B2 | 9/2010 | Bergfjord |
| 7,813,838 B2 | 10/2010 | Sommer |
| 7,818,044 B2 | 10/2010 | Dukesherer et al. |
| 7,819,859 B2 | 10/2010 | Prisco et al. |
| 7,824,401 B2 | 11/2010 | Manzo et al. |
| 7,831,294 B2 | 11/2010 | Viswanathan |
| 7,834,484 B2 | 11/2010 | Sartor |
| 7,835,557 B2 | 11/2010 | Kendrick et al. |
| 7,835,778 B2 | 11/2010 | Foley et al. |
| 7,835,784 B2 | 11/2010 | Mire et al. |
| 7,840,253 B2 | 11/2010 | Tremblay et al. |
| 7,840,256 B2 | 11/2010 | Lakin et al. |
| 7,843,158 B2 | 11/2010 | Prisco |
| 7,844,320 B2 | 11/2010 | Shahidi |
| 7,853,305 B2 | 12/2010 | Simon et al. |
| 7,853,313 B2 | 12/2010 | Thompson |
| 7,865,269 B2 | 1/2011 | Prisco et al. |
| D631,966 S | 2/2011 | Perloff et al. |
| 7,879,045 B2 | 2/2011 | Gielen et al. |
| 7,881,767 B2 | 2/2011 | Strommer et al. |
| 7,881,770 B2 | 2/2011 | Melkent et al. |
| 7,886,743 B2 | 2/2011 | Cooper et al. |
| RE42,194 E | 3/2011 | Foley et al. |
| RE42,226 E | 3/2011 | Foley et al. |
| 7,900,524 B2 | 3/2011 | Calloway et al. |
| 7,907,166 B2 | 3/2011 | Lamprecht et al. |
| 7,909,122 B2 | 3/2011 | Schena et al. |
| 7,925,653 B2 | 4/2011 | Saptharishi |
| 7,930,065 B2 | 4/2011 | Larkin et al. |
| 7,935,130 B2 | 5/2011 | Williams |
| 7,940,999 B2 | 5/2011 | Liao et al. |
| 7,945,012 B2 | 5/2011 | Ye et al. |
| 7,945,021 B2 | 5/2011 | Shapiro et al. |
| 7,953,470 B2 | 5/2011 | Vetter et al. |
| 7,954,397 B2 | 6/2011 | Choi et al. |
| 7,971,341 B2 | 7/2011 | Dukesherer et al. |
| 7,974,674 B2 | 7/2011 | Hauck et al. |
| 7,974,677 B2 | 7/2011 | Mire et al. |
| 7,974,681 B2 | 7/2011 | Wallace et al. |
| 7,979,157 B2 | 7/2011 | Anvari |
| 7,983,733 B2 | 7/2011 | Viswanathan |
| 7,988,215 B2 | 8/2011 | Seibold |
| 7,996,110 B2 | 8/2011 | Lipow et al. |
| 8,004,121 B2 | 8/2011 | Sartor |
| 8,004,229 B2 | 8/2011 | Nowlin et al. |
| 8,010,177 B2 | 8/2011 | Csavoy et al. |
| 8,019,045 B2 | 9/2011 | Kato |
| 8,021,310 B2 | 9/2011 | Sanborn et al. |
| 8,035,685 B2 | 10/2011 | Jensen |
| 8,046,054 B2 | 10/2011 | Kim et al. |
| 8,046,057 B2 | 10/2011 | Clarke |
| 8,052,688 B2 | 11/2011 | Wolf, II |
| 8,054,184 B2 | 11/2011 | Cline et al. |
| 8,054,752 B2 | 11/2011 | Druke et al. |
| 8,057,397 B2 | 11/2011 | Li et al. |
| 8,057,407 B2 | 11/2011 | Martinelli et al. |
| 8,062,288 B2 | 11/2011 | Cooper et al. |
| 8,062,375 B2 | 11/2011 | Glerum et al. |
| 8,066,524 B2 | 11/2011 | Burbank et al. |
| 8,073,335 B2 | 12/2011 | Labonville et al. |
| 8,079,950 B2 | 12/2011 | Stern et al. |
| 8,086,299 B2 | 12/2011 | Adler et al. |
| 8,092,370 B2 | 1/2012 | Roberts et al. |
| 8,098,914 B2 | 1/2012 | Liao et al. |
| 8,100,950 B2 | 1/2012 | St. Clair et al. |
| 8,105,320 B2 | 1/2012 | Manzo |
| 8,108,025 B2 | 1/2012 | Csavoy et al. |
| 8,109,877 B2 | 2/2012 | Moctezuma de la Barrera et al. |
| 8,112,292 B2 | 2/2012 | Simon |
| 8,116,430 B1 | 2/2012 | Shapiro et al. |
| 8,120,301 B2 | 2/2012 | Goldberg et al. |
| 8,121,249 B2 | 2/2012 | Wang et al. |
| 8,123,675 B2 | 2/2012 | Funda et al. |
| 8,133,229 B1 | 3/2012 | Bonutti |
| 8,142,420 B2 | 3/2012 | Schena |
| 8,147,494 B2 | 4/2012 | Leitner et al. |
| 8,150,494 B2 | 4/2012 | Simon et al. |
| 8,150,497 B2 | 4/2012 | Gielen et al. |
| 8,150,498 B2 | 4/2012 | Gielen et al. |
| 8,165,658 B2 | 4/2012 | Waynik et al. |
| 8,170,313 B2 | 5/2012 | Kendrick et al. |
| 8,179,073 B2 | 5/2012 | Farritor et al. |
| 8,182,476 B2 | 5/2012 | Julian et al. |
| 8,184,880 B2 | 5/2012 | Zhao et al. |
| 8,202,278 B2 | 6/2012 | Orban, III et al. |
| 8,208,708 B2 | 6/2012 | Homan et al. |
| 8,208,988 B2 | 6/2012 | Jensen |
| 8,219,177 B2 | 7/2012 | Smith et al. |
| 8,219,178 B2 | 7/2012 | Smith et al. |
| 8,220,468 B2 | 7/2012 | Cooper et al. |
| 8,224,024 B2 | 7/2012 | Foxlin et al. |
| 8,224,484 B2 | 7/2012 | Swarup et al. |
| 8,225,798 B2 | 7/2012 | Baldwin et al. |
| 8,228,368 B2 | 7/2012 | Zhao et al. |
| 8,231,610 B2 | 7/2012 | Jo et al. |
| 8,263,933 B2 | 7/2012 | Hartmann et al. |
| 8,239,001 B2 | 8/2012 | Verard et al. |
| 8,241,271 B2 | 8/2012 | Millman et al. |
| 8,248,413 B2 | 8/2012 | Gattani et al. |
| 8,256,319 B2 | 9/2012 | Cooper et al. |
| 8,271,069 B2 | 9/2012 | Jascob et al. |
| 8,271,130 B2 | 9/2012 | Hourtash |
| 8,281,670 B2 | 10/2012 | Larkin et al. |
| 8,282,653 B2 | 10/2012 | Nelson et al. |
| 8,301,226 B2 | 10/2012 | Csavoy et al. |
| 8,311,611 B2 | 11/2012 | Csavoy et al. |
| 8,320,991 B2 | 11/2012 | Jascob et al. |
| 8,332,012 B2 | 12/2012 | Kienzle, III |
| 8,333,755 B2 | 12/2012 | Cooper et al. |
| 8,335,552 B2 | 12/2012 | Stiles |
| 8,335,557 B2 | 12/2012 | Maschke |
| 8,348,931 B2 | 1/2013 | Cooper et al. |
| 8,353,963 B2 | 1/2013 | Glerum |
| 8,358,818 B2 | 1/2013 | Miga et al. |
| 8,359,730 B2 | 1/2013 | Burg et al. |
| 8,374,673 B2 | 2/2013 | Adcox et al. |
| 8,374,723 B2 | 2/2013 | Zhao et al. |
| 8,379,791 B2 | 2/2013 | Forthmann et al. |
| 8,386,019 B2 | 2/2013 | Camus et al. |
| 8,392,022 B2 | 3/2013 | Ortmaier et al. |
| 8,394,099 B2 | 3/2013 | Patwardhan |
| 8,395,342 B2 | 3/2013 | Prisco |
| 8,398,634 B2 | 3/2013 | Manzo et al. |
| 8,400,094 B2 | 3/2013 | Schena |
| 8,414,957 B2 | 4/2013 | Enzerink et al. |
| 8,418,073 B2 | 4/2013 | Mohr et al. |
| 8,450,694 B2 | 5/2013 | Baviera et al. |
| 8,452,447 B2 | 5/2013 | Nixon |
| RE44,305 E | 6/2013 | Foley et al. |
| 8,462,911 B2 | 6/2013 | Vesel et al. |
| 8,465,476 B2 | 6/2013 | Rogers et al. |

(56) References Cited

U.S. PATENT DOCUMENTS

| | | |
|---|---|---|
| 8,465,771 B2 | 6/2013 | Wan et al. |
| 8,467,851 B2 | 6/2013 | Mire et al. |
| 8,467,852 B2 | 6/2013 | Csavoy et al. |
| 8,469,947 B2 | 6/2013 | Devengenzo et al. |
| RE44,392 E | 7/2013 | Hynes |
| 8,483,434 B2 | 7/2013 | Buehner et al. |
| 8,483,800 B2 | 7/2013 | Jensen et al. |
| 8,486,532 B2 | 7/2013 | Enzerink et al. |
| 8,489,235 B2 | 7/2013 | Moll et al. |
| 8,500,722 B2 | 8/2013 | Cooper |
| 8,500,728 B2 | 8/2013 | Newton et al. |
| 8,504,201 B2 | 8/2013 | Moll et al. |
| 8,506,555 B2 | 8/2013 | Ruiz Morales |
| 8,506,556 B2 | 8/2013 | Schena |
| 8,508,173 B2 | 8/2013 | Goldberg et al. |
| 8,512,318 B2 | 8/2013 | Tovey et al. |
| 8,515,576 B2 | 8/2013 | Lipow et al. |
| 8,518,120 B2 | 8/2013 | Glerum et al. |
| 8,521,331 B2 | 8/2013 | Itkowitz |
| 8,526,688 B2 | 9/2013 | Groszmann et al. |
| 8,526,700 B2 | 9/2013 | Issacs |
| 8,527,094 B2 | 9/2013 | Kumar et al. |
| 8,528,440 B2 | 9/2013 | Morley et al. |
| 8,532,741 B2 | 9/2013 | Heruth et al. |
| 8,541,970 B2 | 9/2013 | Nowlin et al. |
| 8,548,563 B2 | 10/2013 | Simon et al. |
| 8,549,732 B2 | 10/2013 | Burg et al. |
| 8,551,114 B2 | 10/2013 | Ramos de la Pena |
| 8,551,116 B2 | 10/2013 | Julian et al. |
| 8,556,807 B2 | 10/2013 | Scott et al. |
| 8,556,979 B2 | 10/2013 | Glerum et al. |
| 8,560,118 B2 | 10/2013 | Green et al. |
| 8,561,473 B2 | 10/2013 | Blumenkranz |
| 8,562,594 B2 | 10/2013 | Cooper et al. |
| 8,571,638 B2 | 10/2013 | Shoham |
| 8,571,710 B2 | 10/2013 | Coste-Maniere et al. |
| 8,573,465 B2 | 11/2013 | Shelton, IV |
| 8,574,303 B2 | 11/2013 | Sharkey et al. |
| 8,585,420 B2 | 11/2013 | Burbank et al. |
| 8,594,841 B2 | 11/2013 | Zhao et al. |
| 8,597,198 B2 | 12/2013 | Sanborn et al. |
| 8,600,478 B2 | 12/2013 | Verard et al. |
| 8,603,077 B2 | 12/2013 | Cooper et al. |
| 8,611,985 B2 | 12/2013 | Lavallee et al. |
| 8,613,230 B2 | 12/2013 | Blumenkranz et al. |
| 8,621,939 B2 | 1/2014 | Blumenkranz et al. |
| 8,624,537 B2 | 1/2014 | Nowlin et al. |
| 8,630,389 B2 | 1/2014 | Kato |
| 8,634,897 B2 | 1/2014 | Simon et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,639,000 B2 | 1/2014 | Zhao et al. |
| 8,641,726 B2 | 2/2014 | Bonutti |
| 8,644,907 B2 | 2/2014 | Hartmann et al. |
| 8,657,809 B2 | 2/2014 | Schoepp |
| 8,660,635 B2 | 2/2014 | Simon et al. |
| 8,666,544 B2 | 3/2014 | Moll et al. |
| 8,675,939 B2 | 3/2014 | Moctezuma de la Barrera |
| 8,678,647 B2 | 3/2014 | Gregerson et al. |
| 8,679,125 B2 | 3/2014 | Smith et al. |
| 8,679,183 B2 | 3/2014 | Glerum et al. |
| 8,682,413 B2 | 3/2014 | Lloyd |
| 8,684,253 B2 | 4/2014 | Giordano et al. |
| 8,685,098 B2 | 4/2014 | Glerum et al. |
| 8,693,730 B2 | 4/2014 | Umasuthan et al. |
| 8,694,075 B2 | 4/2014 | Groszmann et al. |
| 8,696,458 B2 | 4/2014 | Foxlin et al. |
| 8,700,123 B2 | 4/2014 | Okamura et al. |
| 8,706,086 B2 | 4/2014 | Glerum |
| 8,706,185 B2 | 4/2014 | Foley et al. |
| 8,706,301 B2 | 4/2014 | Zhao et al. |
| 8,717,430 B2 | 5/2014 | Simon et al. |
| 8,727,618 B2 | 5/2014 | Maschke et al. |
| 8,734,432 B2 | 5/2014 | Tuma et al. |
| 8,738,115 B2 | 5/2014 | Amberg et al. |
| 8,738,181 B2 | 5/2014 | Greer et al. |
| 8,740,882 B2 | 6/2014 | Jun et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,761,930 B2 | 6/2014 | Nixon |
| 8,764,448 B2 | 7/2014 | Yang et al. |
| 8,771,170 B2 | 7/2014 | Mesallum et al. |
| 8,781,186 B2 | 7/2014 | Clements et al. |
| 8,781,630 B2 | 7/2014 | Banks et al. |
| 8,784,385 B2 | 7/2014 | Boyden et al. |
| 8,786,241 B2 | 7/2014 | Nowlin et al. |
| 8,787,520 B2 | 7/2014 | Baba |
| 8,792,704 B2 | 7/2014 | Isaacs |
| 8,798,231 B2 | 8/2014 | Notohara et al. |
| 8,800,838 B2 | 8/2014 | Shelton, IV |
| 8,808,164 B2 | 8/2014 | Hoffman et al. |
| 8,812,077 B2 | 8/2014 | Dempsey |
| 8,814,793 B2 | 8/2014 | Brabrand |
| 8,816,628 B2 | 8/2014 | Nowlin et al. |
| 8,818,105 B2 | 8/2014 | Myronenko et al. |
| 8,820,605 B2 | 9/2014 | Shelton, IV |
| 8,821,511 B2 | 9/2014 | von Jako et al. |
| 8,823,308 B2 | 9/2014 | Nowlin et al. |
| 8,827,996 B2 | 9/2014 | Scott et al. |
| 8,828,024 B2 | 9/2014 | Farritor et al. |
| 8,830,224 B2 | 9/2014 | Zhao et al. |
| 8,834,489 B2 | 9/2014 | Cooper et al. |
| 8,834,490 B2 | 9/2014 | Bonutti |
| 8,838,270 B2 | 9/2014 | Druke et al. |
| 8,844,789 B2 | 9/2014 | Shelton, IV et al. |
| 8,855,822 B2 | 10/2014 | Bartol et al. |
| 8,858,598 B2 | 10/2014 | Seifert et al. |
| 8,860,753 B2 | 10/2014 | Bhandarkar et al. |
| 8,864,751 B2 | 10/2014 | Prisco et al. |
| 8,864,798 B2 | 10/2014 | Weiman et al. |
| 8,864,833 B2 | 10/2014 | Glerum et al. |
| 8,867,703 B2 | 10/2014 | Shapiro et al. |
| 8,870,880 B2 | 10/2014 | Himmelberger et al. |
| 8,876,866 B2 | 11/2014 | Zappacosta et al. |
| 8,880,223 B2 | 11/2014 | Raj et al. |
| 8,882,803 B2 | 11/2014 | Iott et al. |
| 8,883,210 B1 | 11/2014 | Truncale et al. |
| 8,888,821 B2 | 11/2014 | Rezach et al. |
| 8,888,853 B2 | 11/2014 | Glerum et al. |
| 8,888,854 B2 | 11/2014 | Glerum et al. |
| 8,894,652 B2 | 11/2014 | Seifert et al. |
| 8,894,688 B2 | 11/2014 | Suh |
| 8,894,691 B2 | 11/2014 | Iott et al. |
| 8,906,069 B2 | 12/2014 | Hansell et al. |
| 8,964,934 B2 | 2/2015 | Ein-Gal |
| 8,992,580 B2 | 3/2015 | Bar et al. |
| 8,996,169 B2 | 3/2015 | Lightcap et al. |
| 9,001,963 B2 | 4/2015 | Sowards-Emmerd et al. |
| 9,002,076 B2 | 4/2015 | Khadem et al. |
| 9,044,190 B2 | 6/2015 | Rubner et al. |
| 9,107,683 B2 | 8/2015 | Hourtash et al. |
| 9,125,556 B2 | 9/2015 | Zehavi et al. |
| 9,131,986 B2 | 9/2015 | Greer et al. |
| 9,215,968 B2 | 12/2015 | Schostek et al. |
| 9,308,050 B2 | 4/2016 | Kostrzewski et al. |
| 9,380,984 B2 | 7/2016 | Li et al. |
| 9,393,039 B2 | 7/2016 | Lechner et al. |
| 9,398,886 B2 | 7/2016 | Gregerson et al. |
| 9,398,890 B2 | 7/2016 | Dong et al. |
| 9,414,859 B2 | 8/2016 | Ballard et al. |
| 9,420,975 B2 | 8/2016 | Gutfleisch et al. |
| 9,492,235 B2 | 11/2016 | Hourtash et al. |
| 9,592,096 B2 | 3/2017 | Maillet et al. |
| 9,750,465 B2 | 9/2017 | Engel et al. |
| 9,757,203 B2 | 9/2017 | Hourtash et al. |
| 9,795,354 B2 | 10/2017 | Menegaz et al. |
| 9,814,535 B2 | 11/2017 | Bar et al. |
| 9,820,783 B2 | 11/2017 | Donner et al. |
| 9,833,265 B2 | 11/2017 | Donner et al. |
| 9,848,922 B2 | 12/2017 | Tohmeh et al. |
| 9,925,011 B2 | 3/2018 | Gombert et al. |
| 9,931,025 B1 | 4/2018 | Graetzel et al. |

(56) References Cited

U.S. PATENT DOCUMENTS

| | | |
|---|---|---|
| 10,034,717 B2 | 7/2018 | Miller et al. |
| 10,039,605 B2 * | 8/2018 | Kostrzewski .......... A61B 17/17 |
| 2001/0036302 A1 | 11/2001 | Miller |
| 2002/0035321 A1 | 3/2002 | Bucholz et al. |
| 2004/0068172 A1 | 4/2004 | Nowinski et al. |
| 2004/0076259 A1 | 4/2004 | Jensen et al. |
| 2005/0096502 A1 | 5/2005 | Khalili |
| 2005/0143651 A1 | 6/2005 | Verard et al. |
| 2005/0171558 A1 | 8/2005 | Abovitz et al. |
| 2006/0100610 A1 | 5/2006 | Wallace et al. |
| 2006/0142657 A1 * | 6/2006 | Quaid ................ A61B 17/1764 |
| | | 600/424 |
| 2006/0173329 A1 | 8/2006 | Marquart et al. |
| 2006/0184396 A1 | 8/2006 | Dennis et al. |
| 2006/0241416 A1 | 10/2006 | Marquart et al. |
| 2006/0291612 A1 | 12/2006 | Nishide et al. |
| 2007/0015987 A1 | 1/2007 | Benlloch Baviera et al. |
| 2007/0021738 A1 | 1/2007 | Hasser et al. |
| 2007/0038059 A1 | 2/2007 | Sheffer et al. |
| 2007/0073133 A1 | 3/2007 | Schoenefeld |
| 2007/0156121 A1 | 7/2007 | Millman et al. |
| 2007/0156157 A1 | 7/2007 | Nahum et al. |
| 2007/0167712 A1 | 7/2007 | Keglovich et al. |
| 2007/0233238 A1 | 10/2007 | Huynh et al. |
| 2007/0270685 A1 * | 11/2007 | Kang ..................... A61B 90/03 |
| | | 600/424 |
| 2008/0004523 A1 | 1/2008 | Jensen |
| 2008/0013809 A1 | 1/2008 | Zhu et al. |
| 2008/0033283 A1 | 2/2008 | Dellaca et al. |
| 2008/0046122 A1 | 2/2008 | Manzo et al. |
| 2008/0082109 A1 | 4/2008 | Moll et al. |
| 2008/0108912 A1 | 5/2008 | Node-Langlois |
| 2008/0108991 A1 | 5/2008 | von Jako |
| 2008/0109012 A1 | 5/2008 | Falco et al. |
| 2008/0144906 A1 | 6/2008 | Allred et al. |
| 2008/0161680 A1 | 7/2008 | von Jako et al. |
| 2008/0161682 A1 | 7/2008 | Kendrick et al. |
| 2008/0177203 A1 | 7/2008 | von Jako |
| 2008/0214922 A1 | 9/2008 | Hartmann et al. |
| 2008/0228068 A1 | 9/2008 | Viswanathan et al. |
| 2008/0228196 A1 | 9/2008 | Wang et al. |
| 2008/0235052 A1 | 9/2008 | Node-Langlois et al. |
| 2008/0269596 A1 | 10/2008 | Revie et al. |
| 2008/0287771 A1 | 11/2008 | Anderson |
| 2008/0287781 A1 | 11/2008 | Revie et al. |
| 2008/0300477 A1 | 12/2008 | Lloyd et al. |
| 2008/0300478 A1 | 12/2008 | Zuhars et al. |
| 2008/0302950 A1 | 12/2008 | Park et al. |
| 2008/0306490 A1 | 12/2008 | Lakin et al. |
| 2008/0319311 A1 | 12/2008 | Hamadeh |
| 2009/0012509 A1 | 1/2009 | Csavoy et al. |
| 2009/0030428 A1 | 1/2009 | Omori et al. |
| 2009/0080737 A1 | 3/2009 | Battle et al. |
| 2009/0185655 A1 | 7/2009 | Koken et al. |
| 2009/0198121 A1 | 8/2009 | Hoheisel |
| 2009/0216113 A1 | 8/2009 | Meier et al. |
| 2009/0228019 A1 | 9/2009 | Gross et al. |
| 2009/0259123 A1 | 10/2009 | Navab et al. |
| 2009/0259230 A1 | 10/2009 | Khadem et al. |
| 2009/0264899 A1 | 10/2009 | Appenrodt et al. |
| 2009/0281417 A1 | 11/2009 | Hartmann et al. |
| 2010/0022874 A1 | 1/2010 | Wang et al. |
| 2010/0039506 A1 | 2/2010 | Sarvestani et al. |
| 2010/0125286 A1 | 5/2010 | Wang et al. |
| 2010/0130986 A1 | 5/2010 | Mailloux et al. |
| 2010/0228117 A1 | 9/2010 | Hartmann |
| 2010/0228265 A1 | 9/2010 | Prisco |
| 2010/0249571 A1 | 9/2010 | Jensen et al. |
| 2010/0274120 A1 | 10/2010 | Heuscher |
| 2010/0280363 A1 | 11/2010 | Skarda et al. |
| 2010/0331858 A1 | 12/2010 | Simaan et al. |
| 2011/0022229 A1 | 1/2011 | Jang et al. |
| 2011/0077504 A1 | 3/2011 | Fischer et al. |
| 2011/0098553 A1 | 4/2011 | Robbins et al. |
| 2011/0137152 A1 | 6/2011 | Li |
| 2011/0213384 A1 | 9/2011 | Jeong |
| 2011/0224684 A1 | 9/2011 | Larkin et al. |
| 2011/0224685 A1 | 9/2011 | Larkin et al. |
| 2011/0224686 A1 | 9/2011 | Larkin et al. |
| 2011/0224687 A1 | 9/2011 | Larkin et al. |
| 2011/0224688 A1 | 9/2011 | Larkin et al. |
| 2011/0224689 A1 | 9/2011 | Larkin et al. |
| 2011/0224825 A1 | 9/2011 | Larkin et al. |
| 2011/0230967 A1 | 9/2011 | O'Halloran et al. |
| 2011/0238080 A1 | 9/2011 | Ranjit et al. |
| 2011/0276058 A1 | 11/2011 | Choi et al. |
| 2011/0282189 A1 | 11/2011 | Graumann |
| 2011/0286573 A1 | 11/2011 | Schretter et al. |
| 2011/0295062 A1 | 12/2011 | Gratacos Solsona et al. |
| 2011/0295370 A1 | 12/2011 | Suh et al. |
| 2011/0306986 A1 | 12/2011 | Lee et al. |
| 2012/0035507 A1 | 2/2012 | George et al. |
| 2012/0046668 A1 | 2/2012 | Gantes |
| 2012/0051498 A1 | 3/2012 | Koishi |
| 2012/0053597 A1 | 3/2012 | Anvari et al. |
| 2012/0059248 A1 | 3/2012 | Holsing et al. |
| 2012/0071753 A1 | 3/2012 | Hunter et al. |
| 2012/0108954 A1 | 5/2012 | Schulhauser et al. |
| 2012/0136372 A1 | 5/2012 | Amat Girbau et al. |
| 2012/0143084 A1 | 6/2012 | Shoham |
| 2012/0184839 A1 | 7/2012 | Woerlein |
| 2012/0197182 A1 | 8/2012 | Millman et al. |
| 2012/0226145 A1 | 9/2012 | Chang et al. |
| 2012/0235909 A1 | 9/2012 | Birkenbach et al. |
| 2012/0245596 A1 | 9/2012 | Meenink |
| 2012/0253332 A1 | 10/2012 | Moll |
| 2012/0253360 A1 | 10/2012 | White et al. |
| 2012/0256092 A1 | 10/2012 | Zingerman |
| 2012/0294498 A1 | 11/2012 | Popovic |
| 2012/0296203 A1 | 11/2012 | Hartmann et al. |
| 2013/0006267 A1 | 1/2013 | Odermatt et al. |
| 2013/0016889 A1 | 1/2013 | Myronenko et al. |
| 2013/0030571 A1 | 1/2013 | Ruiz Morales et al. |
| 2013/0035583 A1 | 2/2013 | Park et al. |
| 2013/0060146 A1 | 3/2013 | Yang et al. |
| 2013/0060337 A1 | 3/2013 | Petersheim et al. |
| 2013/0094742 A1 | 4/2013 | Feilkas |
| 2013/0096574 A1 | 4/2013 | Kang et al. |
| 2013/0113791 A1 | 5/2013 | Isaacs et al. |
| 2013/0116706 A1 | 5/2013 | Lee et al. |
| 2013/0131695 A1 | 5/2013 | Scarfogliero et al. |
| 2013/0144307 A1 | 6/2013 | Jeong et al. |
| 2013/0158542 A1 | 6/2013 | Manzo et al. |
| 2013/0165937 A1 | 6/2013 | Patwardhan |
| 2013/0178867 A1 | 7/2013 | Farritor et al. |
| 2013/0178868 A1 | 7/2013 | Roh |
| 2013/0178870 A1 | 7/2013 | Schena |
| 2013/0204271 A1 | 8/2013 | Brisson et al. |
| 2013/0211419 A1 | 8/2013 | Jensen |
| 2013/0211420 A1 | 8/2013 | Jensen |
| 2013/0218142 A1 | 8/2013 | Tuma et al. |
| 2013/0223702 A1 | 8/2013 | Holsing et al. |
| 2013/0225942 A1 | 8/2013 | Holsing et al. |
| 2013/0225943 A1 | 8/2013 | Holsing et al. |
| 2013/0231556 A1 | 9/2013 | Holsing et al. |
| 2013/0237995 A1 | 9/2013 | Lee et al. |
| 2013/0245375 A1 | 9/2013 | DiMaio et al. |
| 2013/0261640 A1 | 10/2013 | Kim et al. |
| 2013/0272488 A1 | 10/2013 | Bailey et al. |
| 2013/0272489 A1 | 10/2013 | Dickman et al. |
| 2013/0274761 A1 | 10/2013 | Devengenzo et al. |
| 2013/0281821 A1 | 10/2013 | Liu et al. |
| 2013/0296884 A1 | 11/2013 | Taylor et al. |
| 2013/0303887 A1 | 11/2013 | Holsing et al. |
| 2013/0307955 A1 | 11/2013 | Deitz et al. |
| 2013/0317521 A1 | 11/2013 | Choi et al. |
| 2013/0325033 A1 | 12/2013 | Schena et al. |
| 2013/0325035 A1 | 12/2013 | Hauck et al. |
| 2013/0331686 A1 | 12/2013 | Freysinger et al. |
| 2013/0331858 A1 | 12/2013 | Devengenzo et al. |
| 2013/0331861 A1 | 12/2013 | Yoon |
| 2013/0342578 A1 | 12/2013 | Isaacs |
| 2013/0345717 A1 | 12/2013 | Markvicka et al. |
| 2013/0345757 A1 | 12/2013 | Stad |

(56) References Cited

U.S. PATENT DOCUMENTS

| | | |
|---|---|---|
| 2014/0001235 A1 | 1/2014 | Shelton, IV |
| 2014/0012131 A1 | 1/2014 | Heruth et al. |
| 2014/0031664 A1 | 1/2014 | Kang et al. |
| 2014/0046128 A1 | 2/2014 | Lee et al. |
| 2014/0046132 A1 | 2/2014 | Hoeg et al. |
| 2014/0046340 A1 | 2/2014 | Wilson et al. |
| 2014/0049629 A1 | 2/2014 | Siewerdsen et al. |
| 2014/0058406 A1 | 2/2014 | Tsekos |
| 2014/0073914 A1 | 3/2014 | Lavallee et al. |
| 2014/0080086 A1 | 3/2014 | Chen |
| 2014/0081128 A1 | 3/2014 | Verard et al. |
| 2014/0088612 A1 | 3/2014 | Bartol et al. |
| 2014/0094694 A1 | 4/2014 | Moctezuma de la Barrera |
| 2014/0094851 A1 | 4/2014 | Gordon |
| 2014/0096369 A1 | 4/2014 | Matsumoto et al. |
| 2014/0100587 A1 | 4/2014 | Farritor et al. |
| 2014/0121676 A1 | 5/2014 | Kostrzewski et al. |
| 2014/0128882 A1 | 5/2014 | Kwak et al. |
| 2014/0135796 A1 | 5/2014 | Simon et al. |
| 2014/0142591 A1 | 5/2014 | Alvarez et al. |
| 2014/0142592 A1 | 5/2014 | Moon et al. |
| 2014/0148692 A1 | 5/2014 | Hartmann et al. |
| 2014/0163581 A1 | 6/2014 | Devengenzo et al. |
| 2014/0171781 A1 | 6/2014 | Stiles |
| 2014/0171900 A1 | 6/2014 | Stiles |
| 2014/0171965 A1 | 6/2014 | Loh et al. |
| 2014/0180308 A1 | 6/2014 | von Grunberg |
| 2014/0180309 A1 | 6/2014 | Seeber et al. |
| 2014/0187915 A1 | 7/2014 | Yaroshenko et al. |
| 2014/0188132 A1 | 7/2014 | Kang |
| 2014/0194699 A1 | 7/2014 | Roh et al. |
| 2014/0130810 A1 | 8/2014 | Azizian et al. |
| 2014/0221819 A1 | 8/2014 | Sarment |
| 2014/0222023 A1 | 8/2014 | Kim et al. |
| 2014/0228631 A1 | 8/2014 | Kwak et al. |
| 2014/0234804 A1 | 8/2014 | Huang et al. |
| 2014/0257328 A1 | 9/2014 | Kim et al. |
| 2014/0257329 A1 | 9/2014 | Jang et al. |
| 2014/0257330 A1 | 9/2014 | Choi et al. |
| 2014/0275760 A1 | 9/2014 | Lee et al. |
| 2014/0275985 A1 | 9/2014 | Walker et al. |
| 2014/0276931 A1 | 9/2014 | Parihar et al. |
| 2014/0276940 A1 | 9/2014 | Seo |
| 2014/0276944 A1 | 9/2014 | Farritor et al. |
| 2014/0288413 A1 | 9/2014 | Hwang et al. |
| 2014/0299648 A1 | 10/2014 | Shelton, IV et al. |
| 2014/0303434 A1 | 10/2014 | Farritor et al. |
| 2014/0303643 A1 | 10/2014 | Ha et al. |
| 2014/0305995 A1 | 10/2014 | Shelton, IV et al. |
| 2014/0309659 A1 | 10/2014 | Roh et al. |
| 2014/0316436 A1 | 10/2014 | Bar et al. |
| 2014/0323803 A1 | 10/2014 | Hoffman et al. |
| 2014/0324070 A1 | 10/2014 | Min et al. |
| 2014/0330288 A1 | 11/2014 | Date et al. |
| 2014/0364720 A1 | 12/2014 | Darrow et al. |
| 2014/0371577 A1 | 12/2014 | Mallet et al. |
| 2015/0039034 A1 | 2/2015 | Frankel et al. |
| 2015/0085970 A1 | 3/2015 | Bouhnik et al. |
| 2015/0146847 A1 | 5/2015 | Liu |
| 2015/0150524 A1 | 6/2015 | Yorkston et al. |
| 2015/0196261 A1 | 7/2015 | Funk |
| 2015/0213633 A1 | 7/2015 | Chang et al. |
| 2015/0335480 A1 | 11/2015 | Alvarez et al. |
| 2015/0342647 A1 | 12/2015 | Frankel et al. |
| 2016/0005194 A1 | 1/2016 | Schretter et al. |
| 2016/0166329 A1 | 6/2016 | Langan et al. |
| 2016/0235480 A1 | 8/2016 | Scholl et al. |
| 2016/0249990 A1 | 9/2016 | Glozman et al. |
| 2016/0302871 A1 | 10/2016 | Gregerson et al. |
| 2016/0320322 A1 | 11/2016 | Suzuki |
| 2016/0331335 A1 | 11/2016 | Gregerson et al. |
| 2017/0135770 A1 | 5/2017 | Scholl et al. |
| 2017/0143284 A1 | 5/2017 | Sehnert et al. |
| 2017/0143426 A1 | 5/2017 | Isaacs et al. |
| 2017/0156816 A1 | 6/2017 | Ibrahim |
| 2017/0202629 A1 | 7/2017 | Maillet et al. |
| 2017/0212723 A1 | 7/2017 | Atarot et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0231710 A1 | 8/2017 | Scholl et al. |
| 2017/0258426 A1 | 9/2017 | Risher-Kelly et al. |
| 2017/0273748 A1 | 9/2017 | Hourtash et al. |
| 2017/0296277 A1 | 10/2017 | Hourtash et al. |
| 2017/0360493 A1 | 12/2017 | Zucker et al. |

* cited by examiner

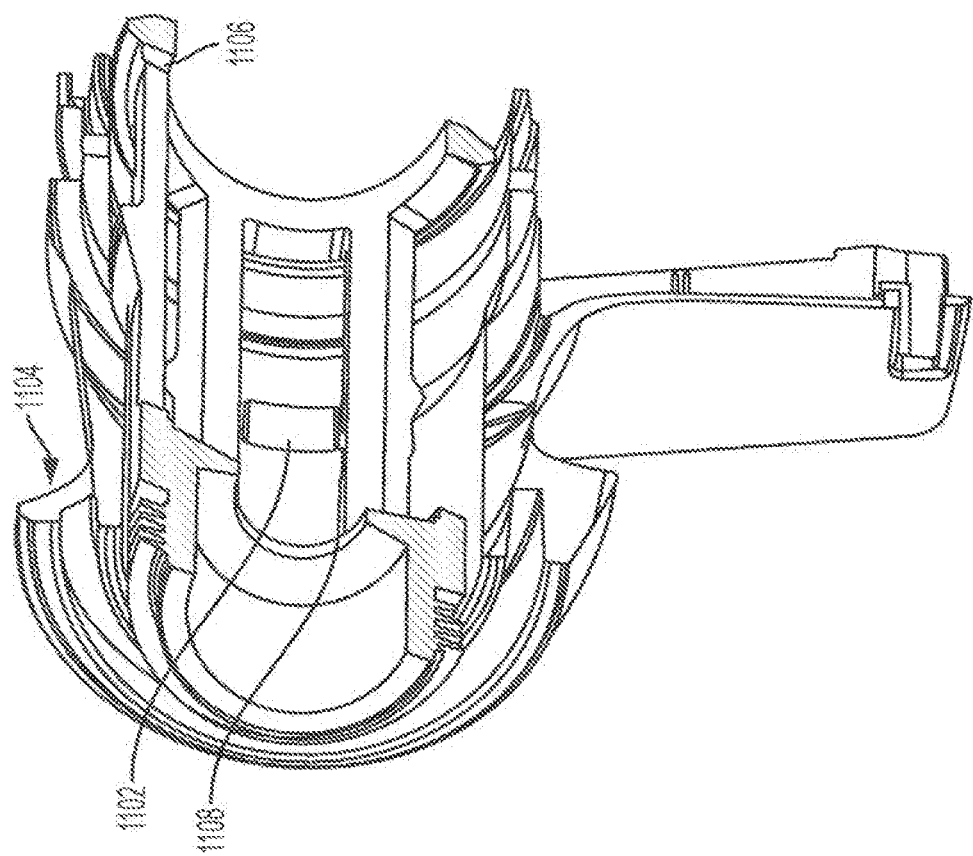

STERILE HANDLE FOR CONTROLLING A ROBOTIC SURGICAL SYSTEM FROM A STERILE FIELD

RELATED APPLICATIONS

The present application is a continuation application of U.S. patent application Ser. No. 14/619,732, filed on Feb. 11, 2015 know U.S. Pat. No. 10,039,605), which claims priority to U.S. Provisional Application No. 61/938,423, filed Feb. 11, 2014 (expired); and U.S. Provisional Application No. 61/950,550, filed Mar. 10, 2014 (expired), the contents of each of which are hereby incorporated by reference in their entireties.

BACKGROUND

Robotic-assisted surgical systems have been developed to improve surgical precision and enable the implementation of new surgical procedures. For example, robotic systems have been developed to sense a surgeon's hand movements and translate them to scaled-down micro-movements and filter out unintentional tremors for precise microsurgical techniques in organ transplants, reconstructions, and minimally invasive surgeries. Other robotic systems are directed to telemanipulation of surgical tools such that the surgeon does not have to be present in the operating room, thereby facilitating remote surgery. Feedback-controlled robotic systems have also been developed to provide smoother manipulation of a surgical tool during a procedure than could be achieved by an unaided surgeon.

However, widespread acceptance of robotic systems by surgeons and hospitals is limited for a variety of reasons. Current systems are expensive to own and maintain. They often require extensive preoperative surgical planning prior to use, and they extend the required preparation time in the operating room. They are physically intrusive, possibly obscuring portions of a surgeon's field of view and blocking certain areas around the operating table, such that a surgeon and/or surgical assistants are relegated to one side of the operating table. Current systems may also be non-intuitive or otherwise cumbersome to use, particularly for surgeons who have developed a special skill or "feel" for performing certain maneuvers during surgery and who find that such skill cannot be implemented using the robotic system. Finally, robotic surgical systems may be vulnerable to malfunction or operator error, despite safety interlocks and power backups.

Spinal surgeries often require precision drilling and placement of screws or other implements in relation to the spine, and there may be constrained access to the vertebrae during surgery that makes such maneuvers difficult. Catastrophic damage or death may result from improper drilling or maneuvering of the body during spinal surgery, due to the proximity of the spinal cord and arteries. Common spinal surgical procedures include a discectomy for removal of all or part of a disk, a foraminotomy for widening of the opening where nerve roots leave the spinal column, a laminectomy for removal of the lamina or bone spurs in the back, and spinal fusion for fusing of two vertebrae or vertebral segments together to eliminate pain caused by movement of the vertebrae.

Spinal surgeries that involve screw placement require preparation of holes in bone (e.g., vertebral segments) prior to placement of the screws. Where such procedures are performed manually, in some implementations, a surgeon judges a drill trajectory for subsequent screw placement on the basis of pre-operative CT scans. Other manual methods which do not involve usage of the pre-operative CT scans, such as fluoroscopy, 3D fluoroscopy or natural landmark-based, may be used to determine the trajectory for preparing holes in bone prior to placement of the screws. In some implementations, the surgeon holds the drill in his hand while drilling, and fluoroscopic images are obtained to verify if the trajectory is correct. Some surgical techniques involve usage of different tools, such as a pedicle finder or K-wires. Such procedures rely strongly on the expertise of the surgeon, and there is significant variation in success rate among different surgeons. Screw misplacement is a common problem in such surgical procedures.

Image-guided spinal surgeries involve optical tracking to aid in screw placement. However, such procedures are currently performed manually, and surgical tools can be inaccurately positioned despite virtual tracking. A surgeon is required to coordinate his real-world, manual manipulation of surgical tools using images displayed on a two dimensional screen. Such procedures can be non-intuitive and require training, since the surgeon's eye must constantly scan both the surgical site and the screen to confirm alignment. Furthermore, procedural error can result in registration inaccuracy of the image-guiding system, rendering it useless, or even misleading.

Certain force feedback systems are used by surgeons in certain procedures; however such systems have a large footprint and take up valuable, limited space in the operating room. These systems also require the use of surgical tools that are specially adapted for use with the force feedback system, and the training required by surgeons to operate such systems can be significant. Moreover, surgeons may not be able to use expertise they have developed in performing spinal surgeries when adapting to use of the current force feedback systems. Such systems, while precise, may require more surgical time and more operating room preparation time to ready placement of the equipment for surgery. Thus, there is a need for systems, apparatus, and methods that provide enhanced precision in performing surgeries such as spinal surgeries.

SUMMARY

Described herein are a sterile handle for use with a robotic surgical system, for example, during spinal surgery. In certain embodiments, the sterile handle adds functionalities and an interface to existing surgical tools such that the robotic system may be commanded from the sterile field during surgery. The sterile handle permits a user, such as a surgeon, to physically manipulate the location of the end-effector of a robotic surgical system from a sterile field.

The sterile handle may include an input device that allows the user to limit the movement of the end-effector, such as limiting the movement to translations or rotations only.

The sterile handle may detect the presence of a user's hand. This ensures the end-effector is only moved when the user manipulates the sterile handle and reduces the likelihood that the end-effector is moved unintentionally. For example, robotic surgical system may permit the movement of the end-effector only in circumstances when the presence detector is activated (e.g., a hand of a surgeon is detected as present because the surgeon is holding the sterile handle).

The sterile handle, in certain embodiments, is configured such that it may be used in a sterile environment.

The design of the sterile handle, in certain embodiments, permits rapid mounting of the handle on a surgical tool.

The sterile handle may be designed to avoid tight spaces between various components of the handle, thereby simply the sterilization process.

The disclosed technology, in certain embodiments, includes a sterile handle for use with a robotic surgical system.

The sterile handle may include a tightening sleeve comprising a hollow tubular structure having a first open end, said structure defining an axis along which a portion of a surgical instrument guide may be inserted into the internal housing. The tightening sleeve may include two or more openings along a length of the tightening sleeve allowing the tightening sleeve to mechanically flex under tension. The openings may be slot, holes, or perforations.

The sterile handle may include a sterile handle housing with a hollow tubular structure having a first open end, said structure defining an axis along which the tightening sleeve may be inserted into the external housing.

In certain embodiments, the sterile handle includes a tightening nut coupled to the sterile handle housing. The tightening nut may include a thread on an interior of the tightening nut. The tightening nut may be configured to engage a thread on exterior of the tightening sleeve and thereby tighten the tightening sleeve such that a diameter of a portion of the tightening sleeve decreases and securely holds a portion of a surgical instrument guide inserted into the internal housing.

The sterile handle may include an electrical assembly that includes one or more input devices for commanding the robotic surgical system. The one or more input devices may be two or more buttons configured to enable a user to place the robotic surgical system in one of a rotation mode, a translation mode, or a combined translation and rotation mode. In certain embodiments, upon selection of a first button of the two or more buttons, the robotic surgical system is in the rotation mode, upon selection of a second button of the two or more buttons, the robotic surgical system is in the translation mode, and upon selection of both the first and second buttons, the robotic surgical system is in the combined translation and rotation mode.

The sterile handle may be ambidextrous such that it may be used on either side of the operating table and/or such that the robotic surgical system may be placed on either side of the operating table.

The sterile handle may be configured to be attached directly or indirectly to an end-effector of the robotic surgical system.

In certain embodiments, the robotic surgical system may be configured to allow robotically-assisted or unassisted positioning and/or movement of the sterile handle by a user with at least six degrees of freedom, wherein the six degrees of freedom are three degrees of translations and three degrees of rotations.

In certain embodiments, the robotic surgical system may be configured to allow robotically-assisted or unassisted positioning and/or movement of the sterile handle by a user with at least four degrees of freedom, wherein the four degrees of freedom are two degrees of translations and two degrees of rotations.

The surgical instrument guide may be configured to hold and/or restrict movement of a second surgical instrument therethrough. The surgical instrument may be a drill bit, tap, screw driver, screw-based implant and awl. The surgical instrument guide may be a drill guide and the surgical instrument may be a drill bit.

The robotic surgical system may be for use in spinal surgery.

The sterile handle may be used in a sterile environment. The sterile handle is at least one of completely or partially disposable.

In some implementations, the sterile handle includes one or more sensors configured to detect a presence of a surgeon's hand in proximity to the sterile handle.

The disclosed technology, in certain embodiments, includes a method of performing surgery with a robotic surgical system. The method may include moving a mobile cart transporting a robotic surgical system comprising a robotic arm in proximity to an operating table, wherein the robotic arm has an end effector with a sterile handle attached thereto.

In certain embodiments, the method includes stabilizing the mobile cart. The method may include maneuvering the robotic arm to a desired position to align an axis defined by the surgical instrument guide at a desired trajectory in relation to a patient situation. In certain embodiments, the method includes fixing the position of the robotic arm (and, therefore, the position of the surgical instrument guide), and maneuvering a surgical instrument in a manner that is constrained by the surgical instrument guide. The method may further include maneuvering the drill bit through the drill bit guide. In certain embodiments, the method may include maneuvering the surgical instrument through the surgical instrument guide.

In some implementations, stabilizing the mobile cart includes extracting one or more rigid legs on the mobile cart such that the mobile cart rests on the one or more rigid legs of the mobile cart. In some implementations, stabilizing the mobile cart includes retracting one or more wheels on the mobile cart such that the mobile cart rests on one or more rigid legs of the mobile cart. In certain embodiments, prior to maneuvering the robotic arm to a desired position, obtaining or accessing a CT scan, 3D CT scan, fluoroscopy, 3D fluoroscopy, or natural landmark-based image of the patient situation.

In some implementations, the sterile handle includes a printed circuit board. The printed circuit board may include the one or more input devices. In some implementations, the sterile handle housing includes one or more ribs that engage one or more openings, respectively, on the tightening sleeve when the sterile handle housing is slide over the tightening sleeve, thereby preventing rotation around the axis of the handle when a torque is applied thereto.

BRIEF DESCRIPTION OF THE FIGURES

The foregoing and other objects, aspects, features, and advantages of the present disclosure will become more apparent and better understood by referring to the following description taken in conjunction with the accompanying drawings, in which:

FIGS. 11A-C are illustrations of portions of an example sterile handle with a rib that engages an opening on the tightening sleeve of the sterile handle;

Figure 1:
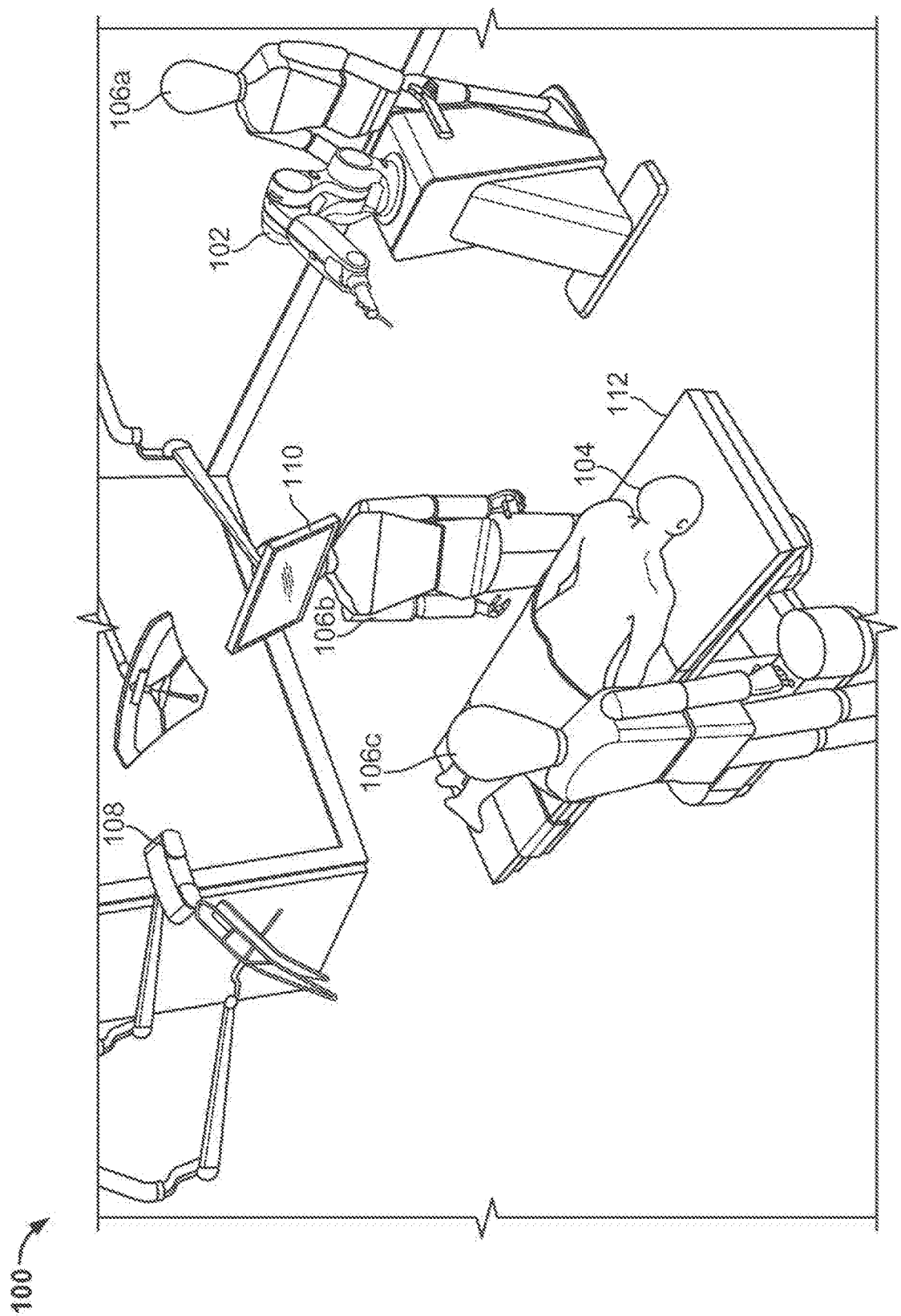
FIG. 1 is an illustration of an example robotic surgical system in an operating room.

The features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements.

DETAILED DESCRIPTION

FIG. 1 illustrates an example robotic surgical system in an operating room 100. In some implementations, one or more surgeons, surgical assistants, surgical technologists and/or other technicians (e.g., 106a-c) perform an operation on a patient 104 using a robotic-assisted surgical system. In the operating room 100 the surgeon may be guided by the robotic system to accurately execute an operation. This may be achieved by robotic guidance of the surgical tools, including ensuring the proper trajectory of the tool (e.g., drill or screw). In some implementations, the surgeon defines the trajectory intra-operatively with little or no pre-operative planning The system allows a surgeon to physically manipulate the tool holder to safely achieve proper alignment of the tool for performing crucial steps of the surgical procedure. Operation of the robot arm by the surgeon (or other operator) in force control mode permits movement of the tool in a measured, even manner that disregards accidental, minor movements of the surgeon. The surgeon moves the tool holder to achieve proper trajectory of the tool (e.g., a drill or screw) prior to operation or insertion of the tool into the patient 104. Once the robotic arm is in the desired position, the arm is fixed to maintain the desired trajectory. The tool holder serves as a stable, secure guide through which a tool may be moved through or slid at an accurate angle. Thus, the disclosed technology provides the surgeon with reliable instruments and techniques to successfully perform his/her surgery.

In some embodiments, the operation may be spinal surgery, such as a discectomy, a foraminotomy, a laminectomy, or a spinal fusion. In some implementations, the surgical robotic system includes a surgical robot 102 on a mobile cart 114. The surgical robot 102 in the example shown in FIG. 1 is positioned in proximity to an operating table 112 without being attached to the operating table 112, thereby providing maximum operating area and mobility to surgeons around the operating table 112 and reducing clutter on the operating table 112. In alternative embodiments, the surgical robot 102 (or cart) is securable to the operating table 112. In certain embodiments, both the operating table 112 and the cart 114 are secured to a common base to prevent any movement of the cart or table 112 in relation to each other, even in the event of an earth tremor.

The mobile cart 114 may permit a user (operator) 106a, such as a technician, nurse, surgeon, or any other medical personnel in the operating room 100, to move the surgical robot 102 to different locations before, during, and/or after a surgical procedure. The mobile cart 104 enables the surgical robot 102 to be easily transported into and out of the operating room 100. For example, a user 106a may move the surgical robot 102 into the operating room 100 from a storage location. In some implementations, the mobile cart 114 may include wheels, a track system, such as a continuous track propulsion system, or other similar mobility systems for translocation of the cart. The mobile cart 114 may include an attached or embedded handle for locomotion of the mobile cart 114 by an operator (e.g., user 106a).

For safety reasons, the mobile cart 114 may be provided with a stabilization system that may be used during a surgical procedure performed with a surgical robot 102. The stabilization mechanism increases the global stiffness of the mobile cart 114 relative to the floor in order to ensure the accuracy of the surgical procedure. In some implementations, the wheels include a locking mechanism that prevents the cart 114 from moving. The stabilizing, braking, and/or locking mechanism may be activated when the machine is turned on. In some implementations, the mobile cart 114 includes multiple stabilizing, braking, and/or locking mechanisms. In some implementations, the stabilizing mechanism is electro-mechanical with electronic activation. The stabilizing, braking, and/or locking mechanism(s) may be entirely mechanical. The stabilizing, braking, and/or locking mechanism(s) may be electronically activated and deactivated.

In some implementations, the surgical robot 102 includes a robotic arm mounted on a mobile cart 114. An actuator may move the robotic arm. The robotic arm may include a force control end-effector configured to hold a surgical tool. The robot 102 may be configured to control and/or allow positioning and/or movement of the end-effector with at least four degrees of freedom (e.g., six degrees of freedom, three translations and three rotations, or four degrees of freedom, two translations and two rotations, or a variation thereof).

In some implementations, the robotic arm is configured to releasably hold a surgical tool, allowing the surgical tool to be removed and replaced with a second surgical tool. The system may allow the surgical tools to be swapped without re-registration, or with automatic or semi-automatic re-registration of the position of the end-effector.

In some implementations, the surgical system includes a surgical robot 102, a tracking detector 108 that captures the position of the patient and different components of the surgical robot 102, and a display screen 110 that displays, for example, real time patient data and/or real time surgical robot trajectories.

In some implementations, a tracking detector 108 monitors the location of patient 104 and the surgical robot 102. The tracking detector 108 may be a camera, a video camera, an infrared detector, field generator and sensors for electromagnetic tracking or any other motion detecting apparatus. In some implementation, based on the patient and robot position, the display screen 110 displays a projected trajectory and/or a proposed trajectory for the robotic arm of robot 102 from its current location to a patient operation site. By continuously monitoring the patient 104 and robotic arm positions, using tracking detector 108, the surgical system can calculate updated trajectories and visually display these trajectories on display screen 110 to inform and guide surgeons and/or technicians in the operating room 100 using the surgical robot. In addition, in certain embodiments, the surgical robot 102 may also change its position and automatically position itself based on trajectories calculated from the real time patient and robotic arm positions captured using the tracking detector 108. For instance, the trajectory of the end-effector can be automatically adjusted in real time to account for movement of the vertebrae and/or other part of the patient 104 during the surgical procedure.

Figure 2:
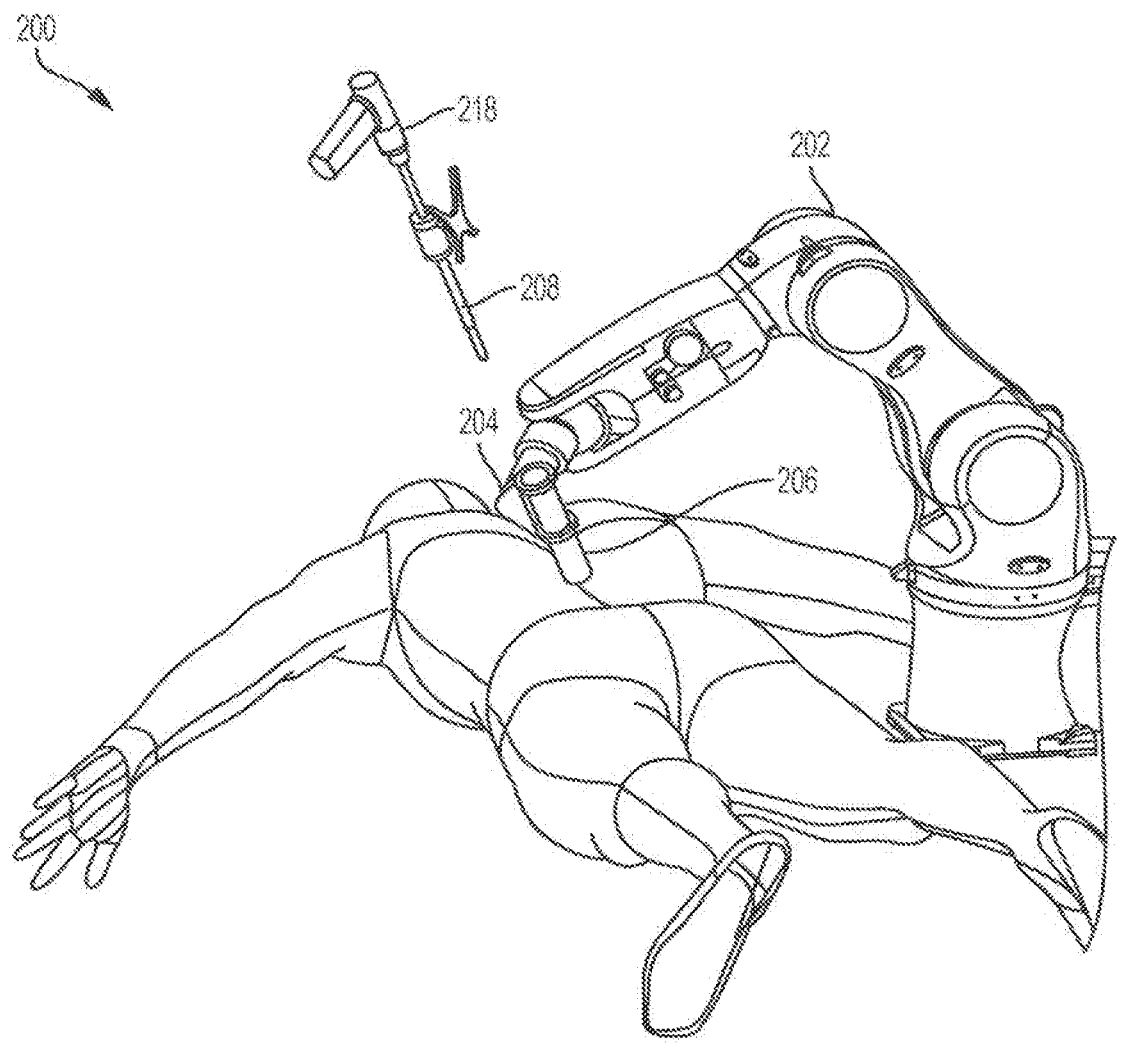
FIG. 2 is an illustration of an example configuration of a robotic arm for performing a surgical operation.

FIG. 2 illustrates an example configuration 200 of a robotic arm for performing a surgical operation. The robotic surgical system includes a robotic arm 202 and an end-effector 204. The manipulator is configured to allow robotically-assisted or unassisted positioning and/or movement of the surgical instrument guide 206 by a user with at least four degrees of freedom to align an axis defined by the instrument guide at a desired trajectory in relation to a patient situation. The axis can be aligned with the desired trajectory in relation to the patient situation via the manipulator.

An end-effector, such as surgical instrument guide 206, is coupled to the end-effector 204 for precisely guiding instruments during surgery. For example, the surgical instrument guide 206 may be coupled to the manipulator via a flange. The surgical instrument guide 206 is configured to hold and/or restrict movement of a surgical instrument therethrough. As shown in FIG. 2, in some implementations, the surgical instrument is a drill 218 and drill bit 208. In this example illustration, the surgical instrument guide 206 is a drill bit guide. Such a system may be used to perform spinal surgery. The surgical tool may be, for example, a tap such as the StealthStation® CR Horizon Legacy Taps from Medtronic, Inc. of Minneapolis, Minn. Other surgical instruments may be used by the system, such as a screw driver, screw-based implant, or awl. For example, the surgical instrument guide may be configured to be used to guide a screw implant and a tissue protector.

Figure 3A:
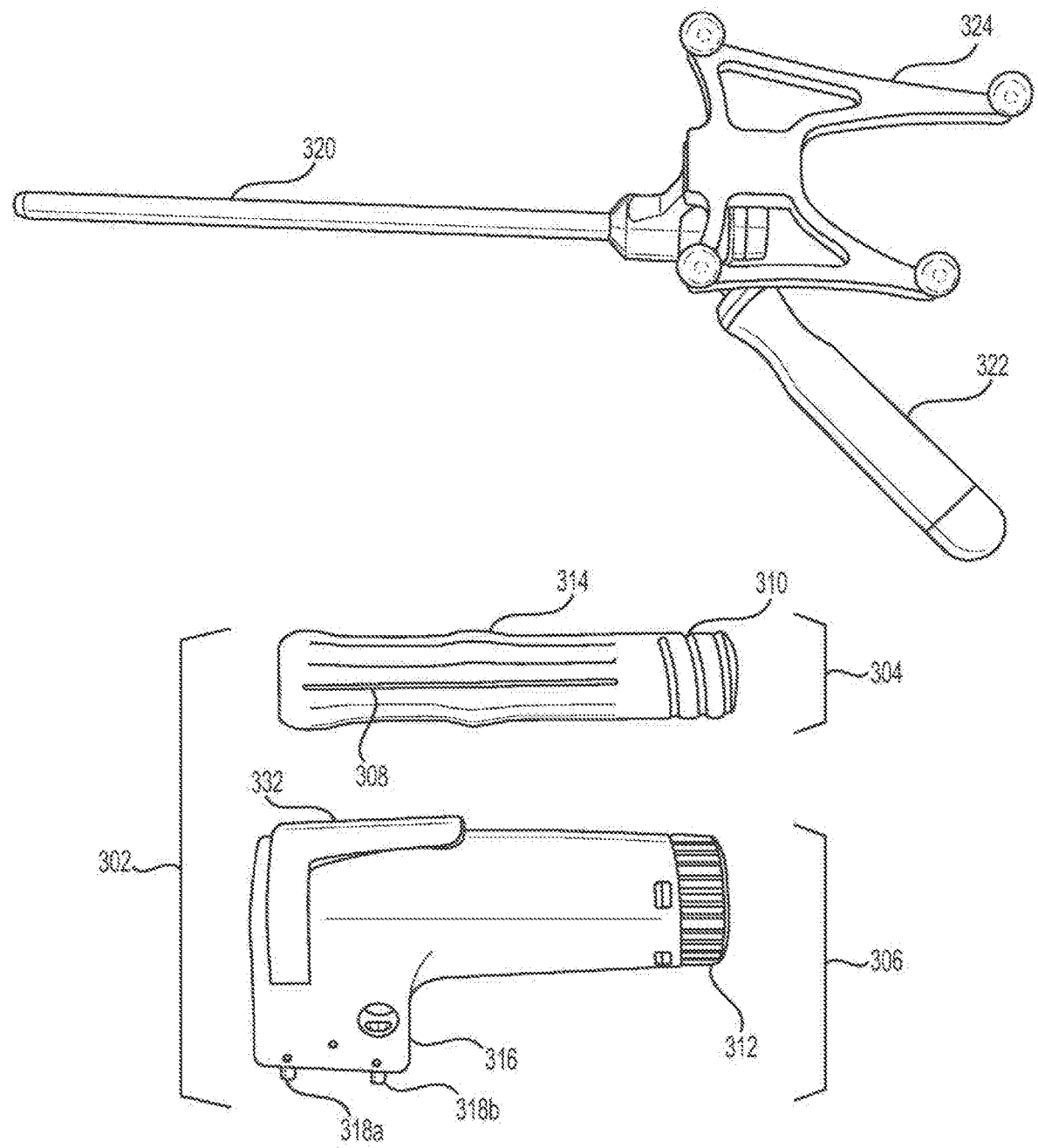
FIGS. 3A through 3C are illustrations of a surgical instrument guide and a sterile handle for use with a robotic surgical system.
Figure 3B:
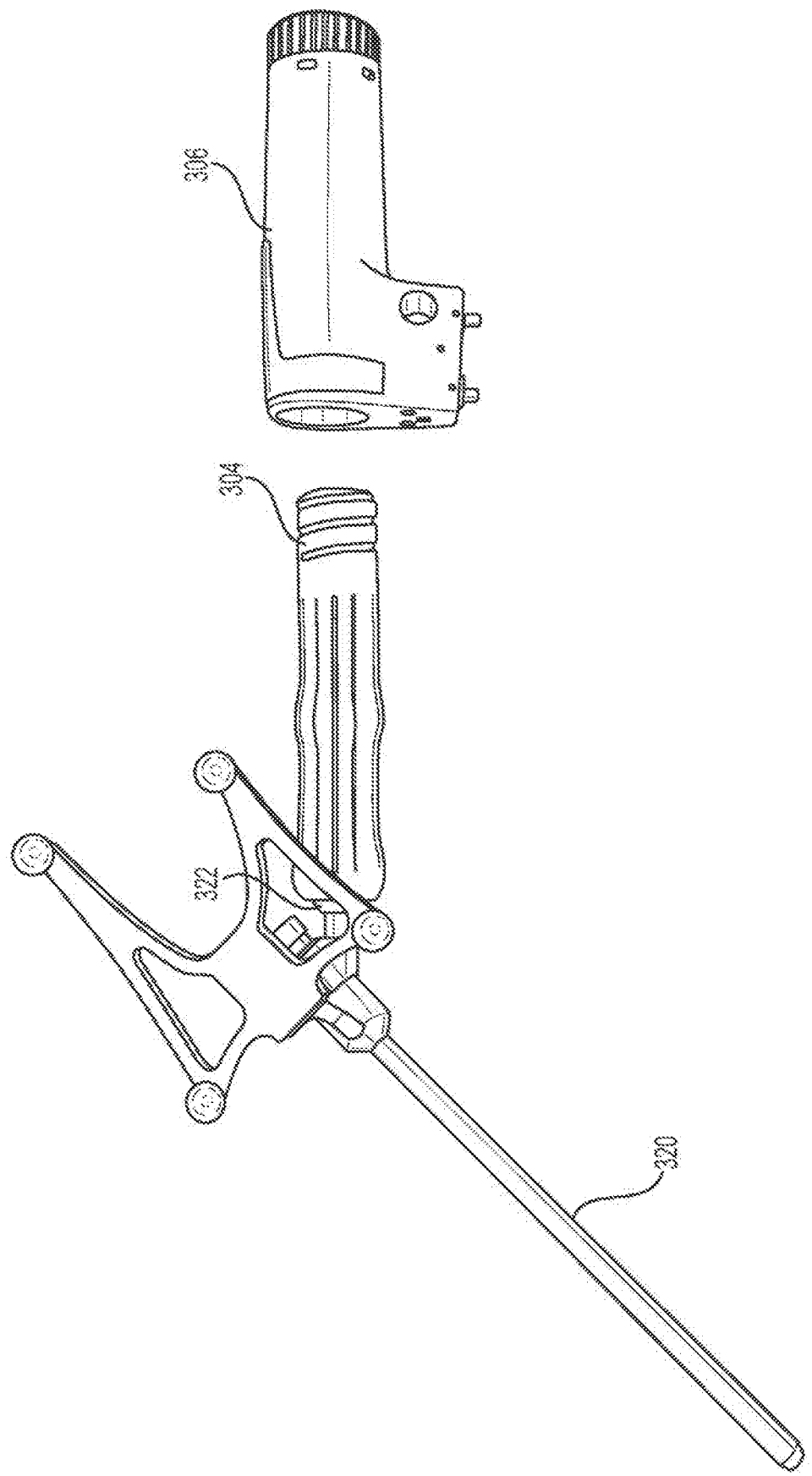
Figure 3C:
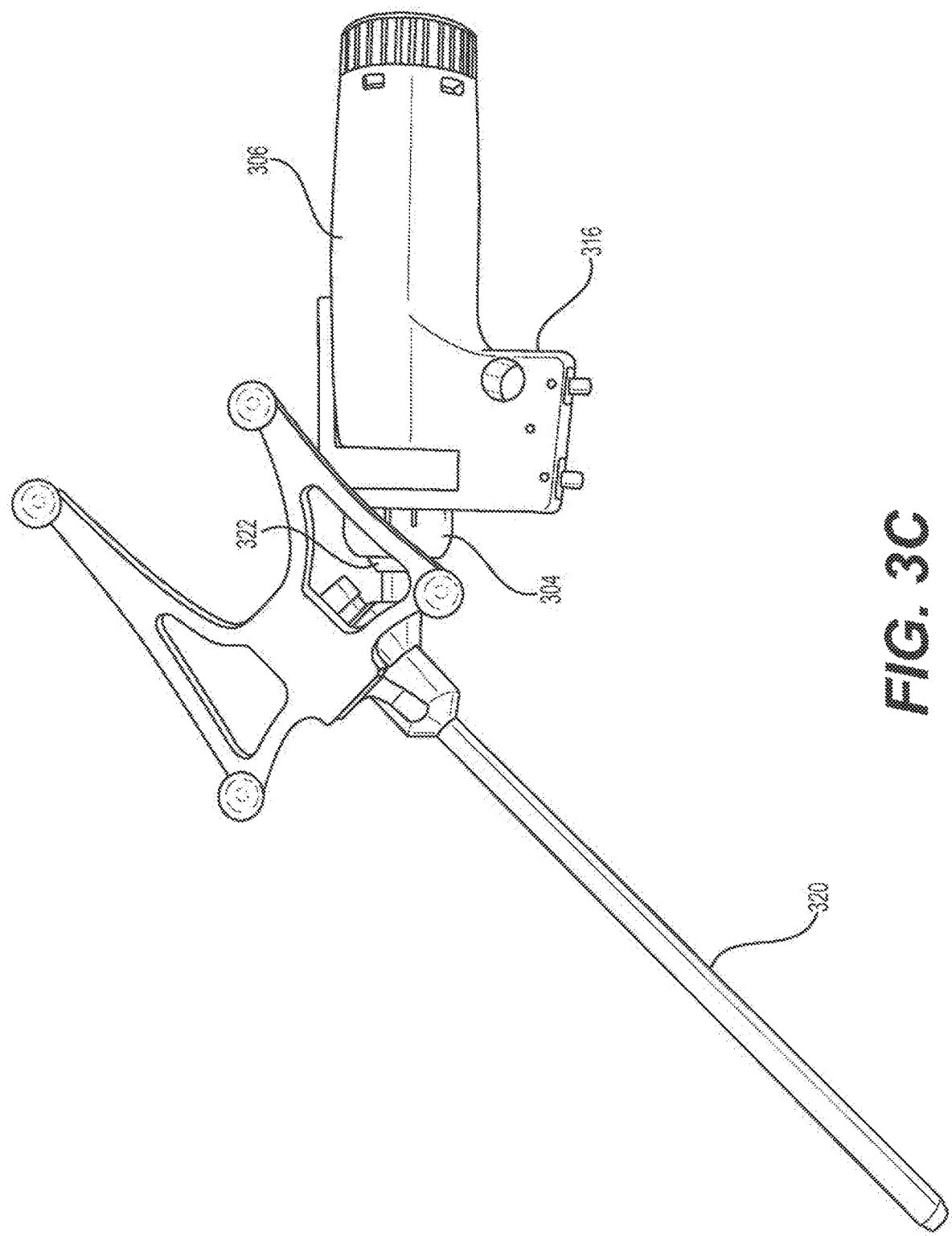

FIGS. 3A through 3C are illustrations of a surgical instrument guide and a sterile handle for use with a robotic surgical system. In some implementations, the sterile handle 302 includes a tightening sleeve 304 with a hollow tubular structure having a first open end. In some implementations, the structure of the tightening sleeve 304 defines an axis along which a portion 322 of a surgical instrument guide 320 may be inserted into the tightening sleeve 304. The portion 322 of the surgical instrument guide 320 that may be inserted into the tightening sleeve 304 may be a separate component (e.g., a handle) that can be mechanically attached to the surgical instrument guide 320. In some implementations, portion 322 of the surgical instrument guide 320 that may be inserted into the tightening sleeve 304 is an integrated component of the surgical instrument guide 320. In some implementations, a navigation tracker 324 is coupled to the surgical instrument guide 320 such that the position of the surgical instrument guide 320 may be tracked by a navigation system (e.g., tracking camera) of the robotic surgical system.

A sterile handle housing 306 may include a hollow tubular structure having a first open end. The sterile handle housing 306 structure may define an axis along which the tightening sleeve 304 may be inserted into the sterile handle housing 306.

The tightening sleeve 304 may include two or more openings 308 along a length of the tightening sleeve allowing the tightening sleeve to mechanically flex under tension. In some implementations, the two or more openings are two or more slots, holes, or perforations.

A tightening nut 312 may be permanently and removably coupled to the sterile handle housing 306. The tightening nut 312 includes a thread on an interior of the tightening nut. The tightening nut 312 is configured to engage a thread 310 on exterior of the tightening sleeve 304 and thereby tighten the tightening sleeve 304 such that a diameter of a portion of the tightening sleeve decreases and securely holds a portion 322 of a surgical instrument guide 320 inserted into the tightening sleeve 304. The tightening sleeve 304 includes a wedge 314 that engages a wedge on the interior of the sterile handle housing 306 as the tightening nut 312 is tightened and the threads inside the tightening nut 312 engage the threads 310 on the tightening sleeve 304 and pull the tightening sleeve in the direction of the tightening nut 312. The wedges force the tightening sleeve to flex and increase the friction between the portion 322 of the surgical instrument holder 320 and the tightening sleeve 304 when the sterile handle 302 is assembled with the portion 322 of the surgical instrument holder 320 inserted into the tightening sleeve 304. Thus, tightening the tightening nut 312 enables the sterile handle to securely hold the surgical instrument guide.

In some implementations, the sterile handle 302 includes an electrical assembly 316. The electrical assembly 316 may include one or more input devices 318 for commanding the robotic surgical system. The one or more input devices 318 may include two or more buttons 318a and 318b configured to enable a user to place the robotic surgical system in one of a rotation mode, a translation mode, or a combined translation and rotation mode. In some implementations, upon selection of a first button 318a of the two or more buttons, the robotic surgical system is in the rotation mode, upon selection of a second button 318b of the two or more buttons, the robotic surgical system is in the translation mode, and upon selection of both the first and second buttons 318a-b, the robotic surgical system is in the combined translation and rotation mode. In some implementations, the handle 302 and input device(s) thereon (e.g., buttons) can be used for instructing the robotic system to translate along a line when the translation button is pressed, rotate around the line if the rotation button is pressed, and/or translate and rotate around the line if both buttons are pressed.

The electrical assembly 316 may be directly integrated into the sterile handle 302. In some implementations, the electrical assembly 316 can be done separately (e.g., using over-molding on buttons and cable or epoxy resin to form an assembly which is integrated into the handle using a rapid locking mechanism).

In some implementations, the sterile handle 302 is ambidextrous. In some implementations, the sterile handle 302 is configured such that a robotic surgical system may be used on either side of an operating table when the handle 302 is in use. The sterile handle 302 is configured to be attached directly or indirectly to an end-effector of the robotic surgical system. In some implementations, the robotic surgical system is configured to allow robotically-assisted or unassisted positioning and/or movement of the sterile handle by a user with at least six degrees of freedom. The six degrees of freedom may be three degrees of translations and three degrees of rotations.

As described above, the sterile handle 302 is configured to securely hold a surgical instrument guide 320. The surgical instrument guide 320 is configured to hold and/or restrict movement of a surgical instrument therethrough. The surgical instrument may be a drill bit, tap, screw driver, screw-based implant, or awl. In some implementations, the surgical instrument guide 320 is a drill guide and the surgical instrument is a drill bit. In some implementations, the robotic surgical system is for use in spinal surgery.

The sterile handle 302 may be completely or partially disposable. For example, in some implementations, the electrical assembly 316 may be disposable. All disposable parts may be produced in molded plastic. In some implementations, reusable parts may be made of either metal or plastic. In some implementations, the entire sterile handle 302 is reusable. Assembly of the sterile handle 302 may be performed pre-operatively. For example, a disposable sterile handle 302 may be completely assembled in the packaging. In some implementations, the sterile handle 302 may be assembled intra-operatively. In some implementations, the electrical assembly 316 may be fixed in the handle before mounting the sterile handle 302 on the surgical instrument 320.

The sterile handle 302 may be made of a sterile material or a material that may be sterilized. In some implementations, the sterile handle 302 may be sterilized using different technologies, such as using Ethylene Oxide (EtO), autoclave, radiation, or other sterilization methods. Different components of the sterile handle 302 using different technologies, for example, mechanical assembly in an autoclave, electrical assembly in an EtO. In some implementations, sterilization is achieved by draping. In some implementations, the sterile handle comprises one or more sensors configured to detect a presence of a surgeon's hand in proximity to the sterile handle. In some implementations, the one or more sensors include a presence mechanism 332 that is engaged by a surgeon's hand when the surgeon holds the handle such that presence of the hand is detected. The presence mechanism may be a lever-button mechanism. In some implementations, the presence mechanism 332 includes one or more capacitive or resistive sensors, or a combination thereof.

FIG. 3B illustrates a handle 322 of a surgical instrument guide 320 with the tightening sleeve 304 of a sterile handle 302 slide over the handle 322. The sterile handle housing 306 is shown adjacent the tightening sleeve 304 and may be slide over the tightening sleeve 304. FIG. 3C illustrates a handle 322 of a surgical instrument guide 320 with the tightening sleeve 304 of a sterile handle 302 slide over the handle 322 and the sterile handle housing 306 slide over the tightening sleeve 304. As the tightening nut 312 is tightened, the body of the tightening sleeve 304 is pinched, thus increasing the friction between the handle 322 and the tightening sleeve 304 and securing the handle 322 within the tightening sleeve 304.

Figure 4:
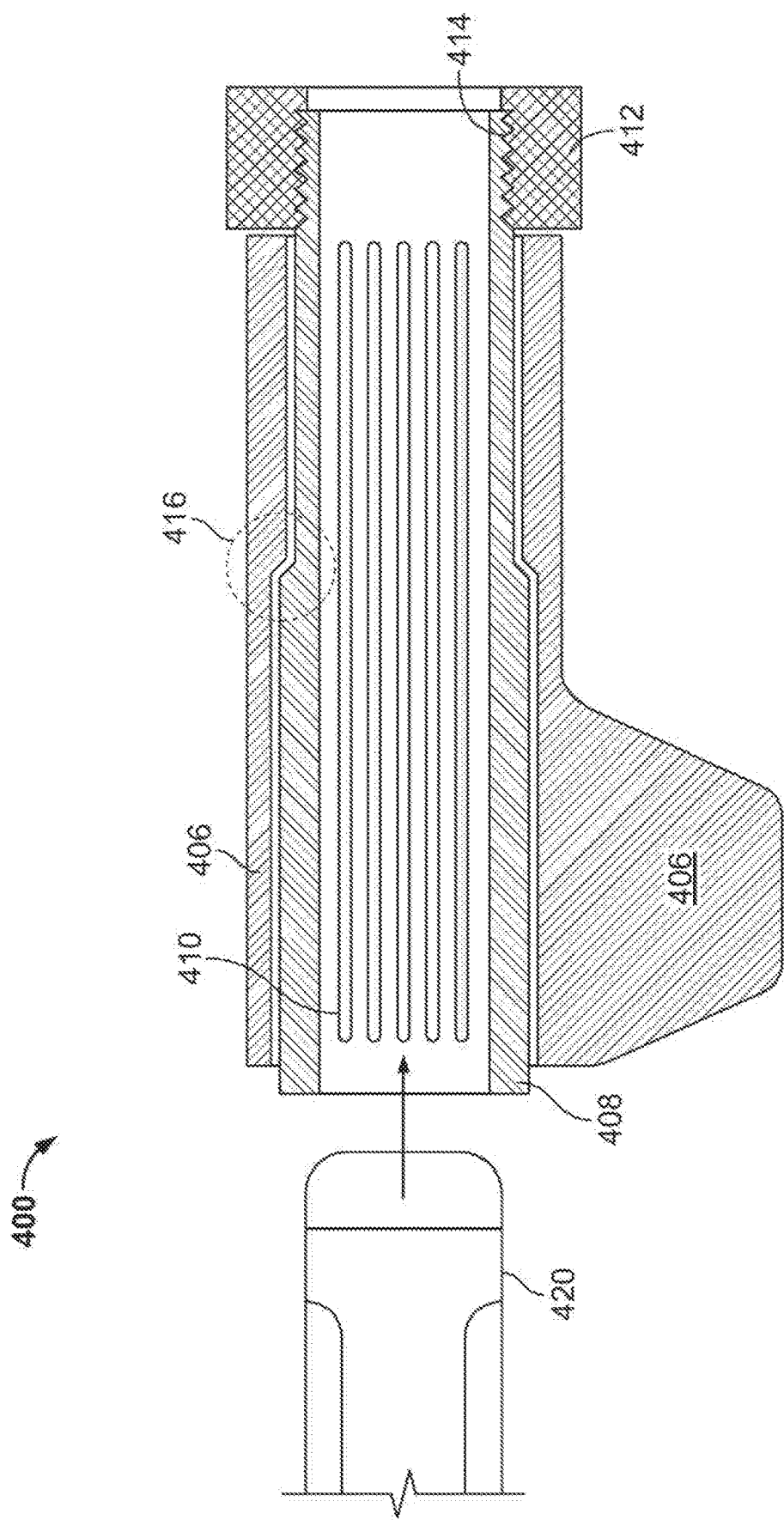
FIG. 4 is an illustration of a cross-sectional view of an example sterile handle with a tightening sleeve and a sterile handle housing.

FIG. 4 illustrates a cross-sectional view of an example sterile handle 400 with a tightening sleeve 408 and a sterile handle housing 406. A surgical instrument guide 420 (e.g., a handle of a surgical instrument guide), may slide into the tightening sleeve 408. As a user tightens the tightening nut 412, threads 414 (e.g., threads on the sterile handle housing 406 and threads on the tightening sleeve 408) cause the tightening sleeve 408 to pull/slide towards the tightening nut 412 (e.g., towards the right as shown in FIG. 4).

The internal housing, in some implementations, includes openings 410 (e.g., slots, holes, or perforations) that allow a portion of the body of the tightening sleeve 408 to be pinched. As the tightening nut 412 is tightened, a wedge 416 causes a portion of the body of the tightening sleeve 408 to be pinched. As shown in FIG. 4, as the tightening sleeve slides to the right, a wedge on the sterile handle housing 406 contacts a wedge on the tightening sleeve 408, thus a portion of the body of the tightening sleeve 408 is pinched. When a surgical instrument guide 420 is inserted into an assembled handle 400 and the tightening nut 412 is tightened, the tightening sleeve 408 "grips" the surgical instrument guide 420 (e.g., the friction between the guide 420 and the tightening sleeve 408 is increased). Thus, the surgical handle 400 securely holds the guide 420.

Figure 5:
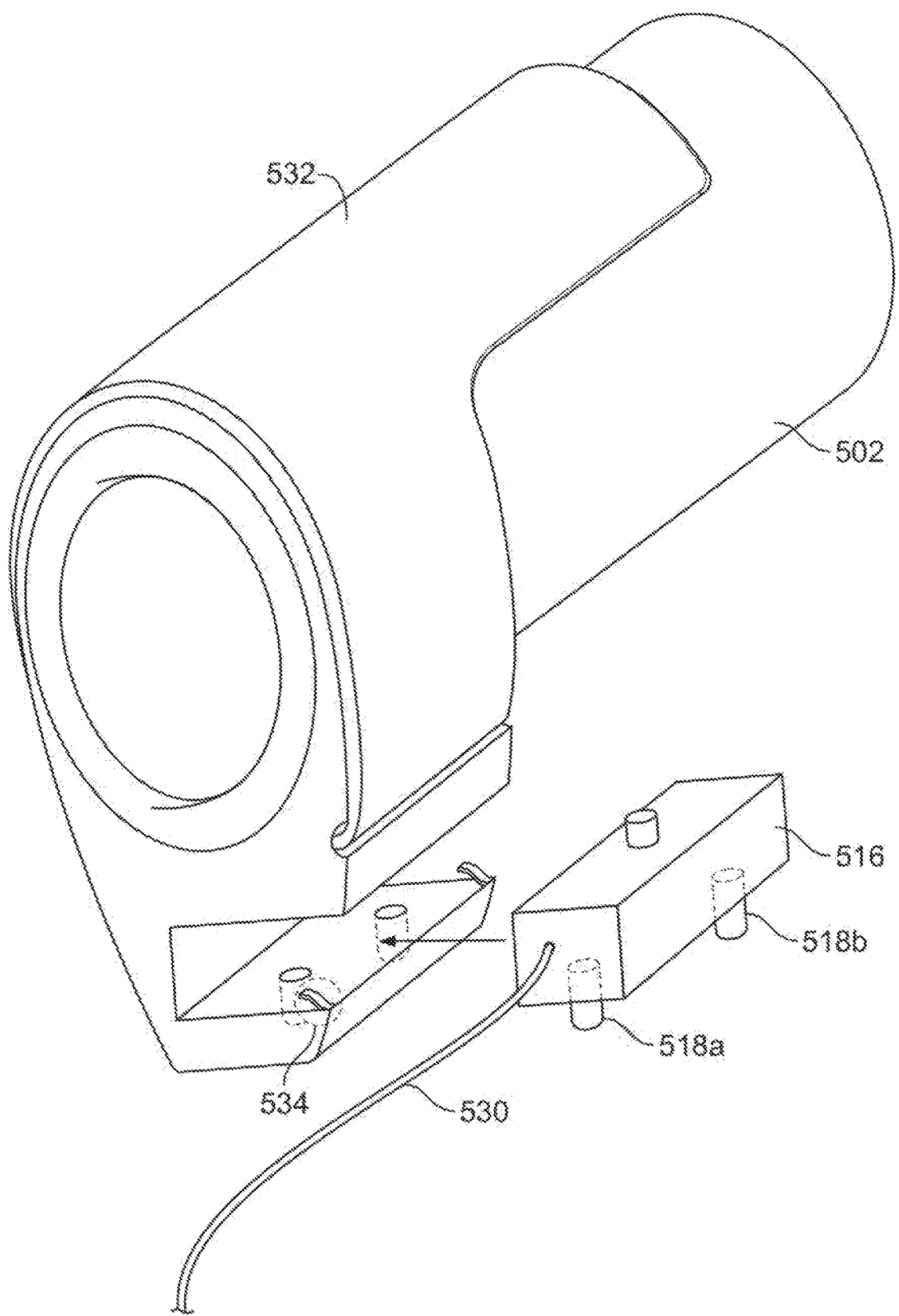
FIG. 5 is an illustration of an example sterile handle for use with a robotic surgical system.

FIG. 5 is an illustration of an example sterile handle for use with a robotic surgical system. In some implementations, the sterile handle 502 includes an electrical assembly 516. The electrical assembly 516 may include one or more input devices 518 for commanding the robotic surgical system. The one or more input devices 518 may include two or more buttons 518a and 518b configured to enable a user to place the robotic surgical system in one of a rotation mode, a translation mode, or a combined translation and rotation mode. In some implementations, upon selection of a first button 518a of the two or more buttons, the robotic surgical system is in the rotation mode, upon selection of a second button 518b of the two or more buttons, the robotic surgical system is in the translation mode, and upon selection of both the first and second buttons 518a-b, the robotic surgical system is in the combined translation and rotation mode. In some implementations, the electrical assembly 516 is integrated into a housing of the sterile handle 502. In some implementations, the electrical assembly 516 is removable. The handle 502 may include a rapid locking mechanism 534 that is used to attach the electrical assembly 516 to the handle 502. The electrical assembly 516 may include a wire 530 that is used to connect to the electrical system of the robotic surgical system. In some implementations, the wire 530 includes a plug that plugs into an embedded connector in a sterile drape (e.g., drape connector).

In some implementations, the sterile handle comprises one or more sensors configured to detect the presence of a surgeon's hand in proximity to the sterile handle. In some implementations, the one or more sensors include a mechanism 332 that is engaged by a surgeon's hand when the surgeon holds the handle such that presence of the hand is detected.

Figure 6:
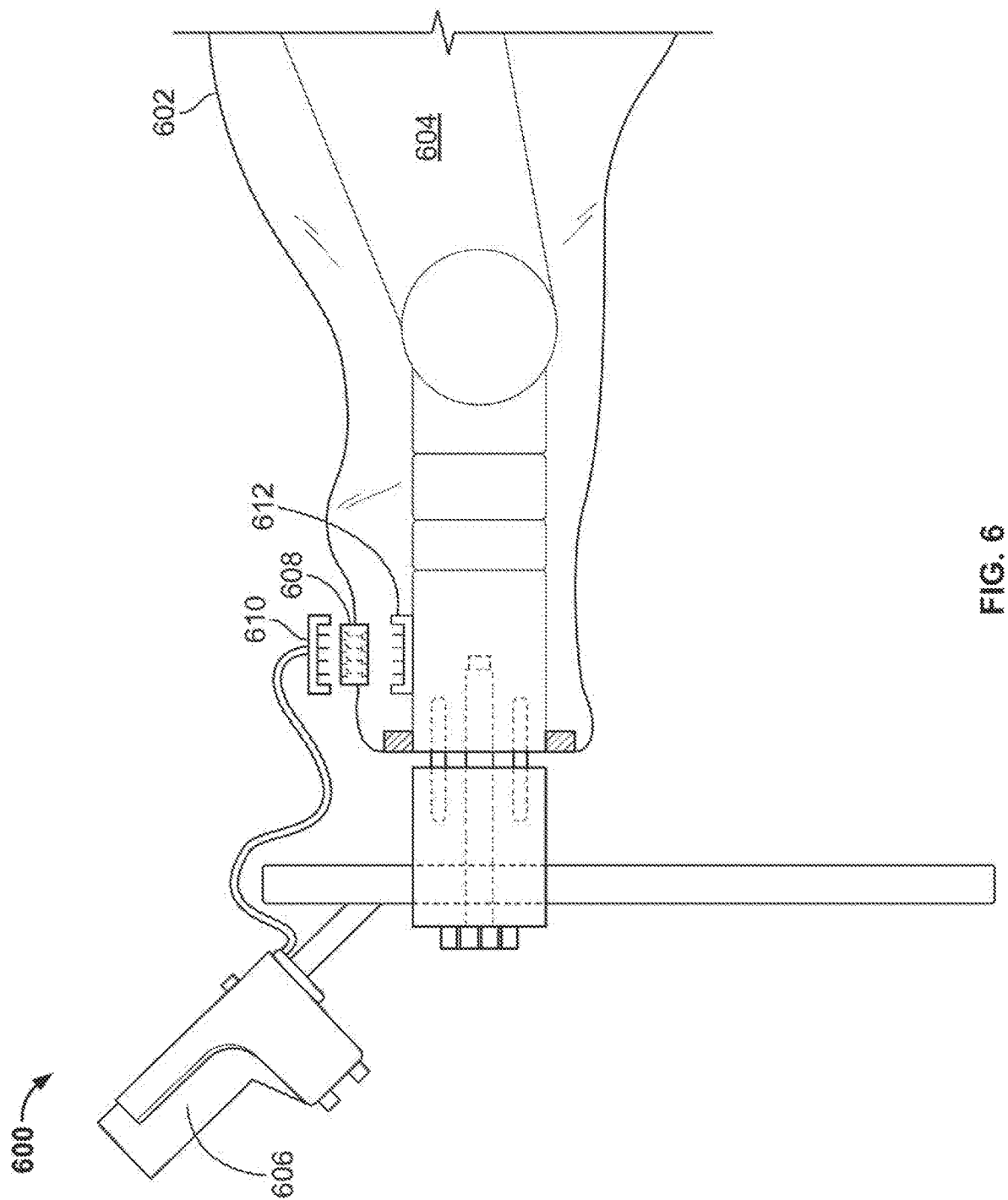
FIG. 6 is an illustration of an example system sterile handle and tool holder attached to a robotic arm.

FIG. 6 illustrates an example system 600 sterile handle and tool holder attached to a robotic arm. In some implementations, the system 600 includes a sterile drape 602 for covering a surgical robotic arm 604 and preventing contamination of a sterile field.

In some implementations, the sterile drape 602 includes a flexible covering with a sterile outer surface. The sterile drape may be partially conformable to a surgical robotic arm. The sterile drape may include an embedded connector 608 configured (e.g., positioned on the flexible covering and sized) to permit electrical contact between the surgical robotic arm 604 (e.g., an actuator of the robotic arm) and a sterile manipulator 606 (e.g., sterile handle) of the robotic arm 604 when the sterile manipulator 606 is separated from the surgical robotic arm by the flexible covering. In some implementations, the sterile drape 602 is disposable (e.g., a single-use product).

The drape connector 608 may be configured to couple to a handle connector 610 that is connected to the sterile handle 606. The drape connector 608 may also be configured to couple to a robot connector 612 that is connected to the electrical system of the robotic surgical system. Thus, the drape connector may act as an intermediary connector that allows the handle to be electrically connected to the electrical system of the robotic surgical system through the sterile drape 602.

Figure 7:
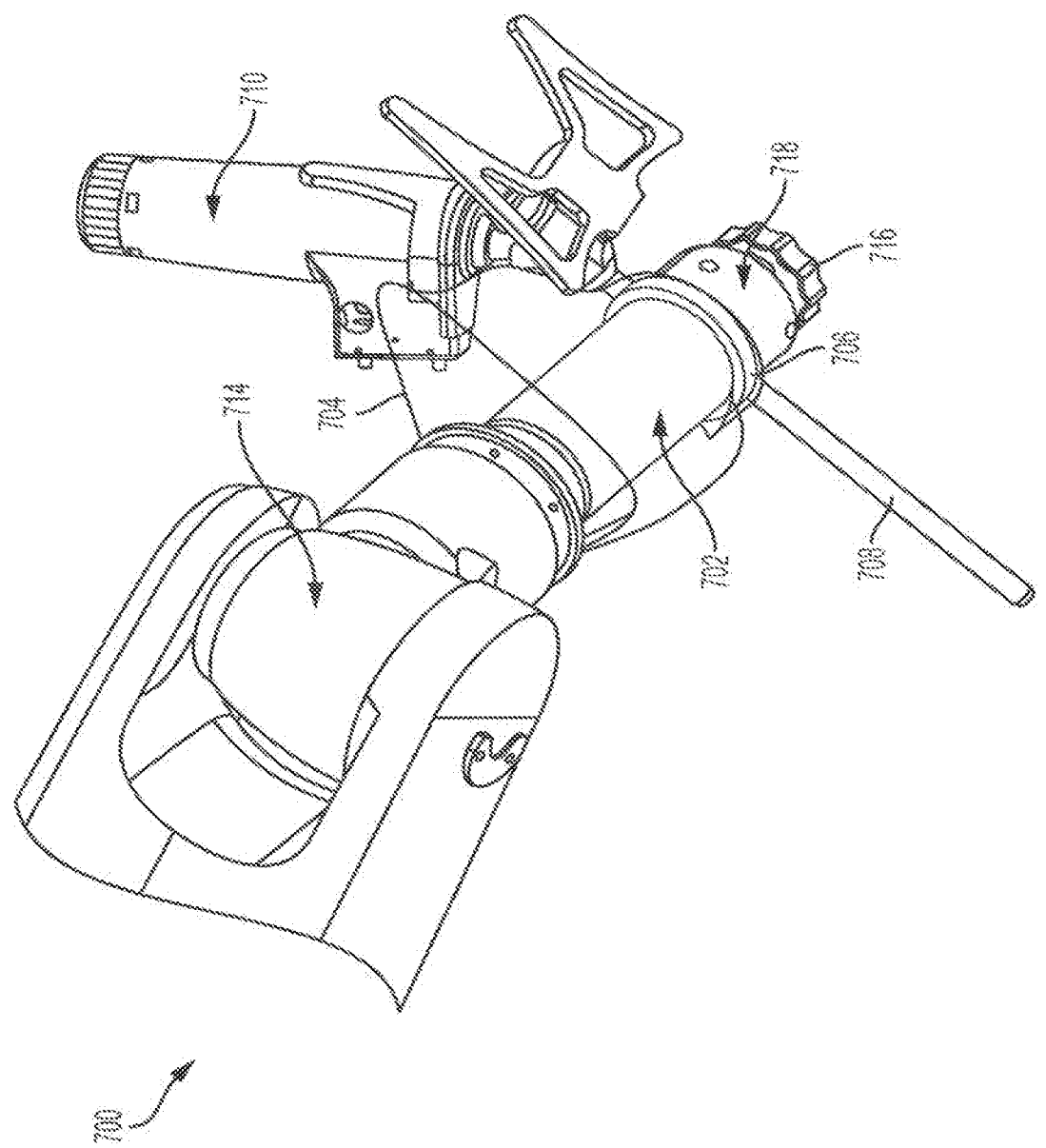
FIG. 7 is an illustration of an example robotic surgical system with a sterile handle.

FIG. 7 is an illustration of an example robotic surgical system 700 with a sterile handle 710. In some implementations, the robotic surgical system is for performing surgery, such as spinal surgery. The robotic surgical system may include a robotic arm 714 with an interface 702 for engaging a sterile adapter 706. The sterile adapter 706 may be configured to attach to the robotic arm 714 via a robotic interface 706 and tightly stretch the sterile drape 704 to assure repeatable and rigid positioning of the sterile drape 704. The sterile drape 704 may be configured to protect the robotic arm from contaminating a sterile field. In some implementations, the sterile drape includes a drape connector configured to electrically couple, through the sterile drape, the manipulator to an electrical system of the robotic surgical system covered by the sterile drape. The sterile handle 710 may be coupled to a handle connector via a cable and the handle connector is configured to electrically connect to the drape connector. The electrical system of the robotic surgical system may be coupled to a robot connector and the robot connector may be configured to electrically connect to the drape connector. Thus, the robot connector may electrically couple the drape connector to the robot connector, through the sterile drape 704.

In some implementations, a surgical instrument holder 718 is configured to securely hold the surgical instrument 708. The surgical instrument holder 718 may be attached to the interface 702 via a tightening screw 716. The tightening screw 716 may protrude through the sterile drape 704 that is tightly stretched over the opening of the sterile adapter 706. The robot interface 702 may include one or more positioning elements 712 (e.g., pegs or pins) configured to provide accurate and repeatable positioning of the surgical instrument holder 714 in reference to the robotic arm. The one or more positioning elements 712 may be round or oblong. The surgical instrument holder 718 may include one or more studs or holes that engage the one or more positioning elements 712. The one or more positioning elements 712 may protrude through the sterile drape 704 when the sterile adapter 706 is attached to the interface 702. In some implementations, the one or more positioning elements 712 extend from the robotic arm 714 and engage one or more surgical instrument holder positioning members. For example, the one or more positioning elements 712 may be the one or more pegs are configured to extend from the robotic arm and engage one or more holes in the surgical instrument holder 718.

In some implementations, the robotic surgical system includes a manipulator 710 (e.g., a sterile handle) configured to allow robotically-assisted or unassisted positioning and/or movement of the surgical instrument by a user with at least four degrees of freedom to align an axis defined by the surgical instrument at a desired trajectory in relation to a patient situation.

In some implementations, the surgical instrument is a surgical instrument guide configured to hold and/or restrict movement of a second surgical instrument there through. The second surgical instrument may be a drill bit, tap, screw driver, screw-based implant, or awl. For example, in the case of spinal surgery, the second surgical instrument may be a drill bit and the surgical instrument guide may be a drill guide.

In some implementations, the robotic surgical system includes a mobile cart configured to transport the robotic surgical system. The sterile drape may be configured to protect the mobile cart from contaminating a sterile field. In some implementations, the sterile drape includes a first sterile drape to protect the robotic arm 714 and a second sterile drape to protect the mobile cart. In some implementations, the sterile drape may include printed marks configured to assist in proper draping procedure. In some implementations, the drape may be folded in a configuration that makes for easily applying the drape to the robotic system.

In some implementations, the surgical instrument holder is configured to be attached to the robotic arm using a fastening system. The fastening system may be a bolt, nut, screw, or one or more electro magnets.

In some implementations, one or more holding stripes are configured to hold the sterile drape. The one or more holding stripes may secure a portion of the sterile drape to the robotic arm. In some implementations, the system includes a suppression system configured to remove air from under the sterile drape. The suppression system may include a ventilator or a suction device that pumps out the air from under the sterile drape.

In some implementations, the surgical instrument holder 714 is made from a non-conductive material (e.g., plastic). The holder 718 may act as an insulator (prevent electrical conductivity) between the surgical instrument 708 and the robotic arm 714. In some implementations, the surgical instrument holder 718 is conductive, however, a non-conducive pad is placed between the holder 718 and the interface 702.

Figure 8:
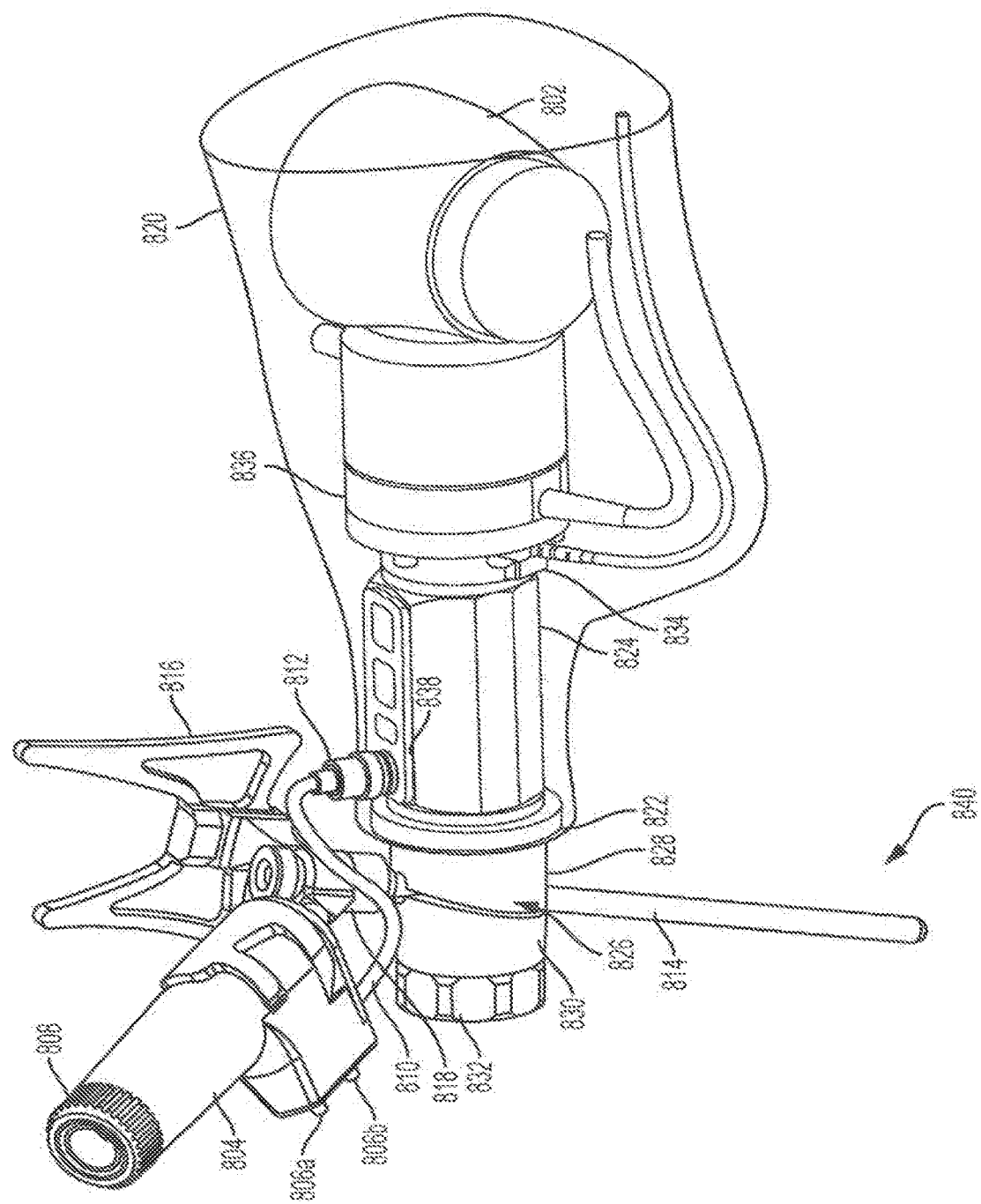
FIG. 8 is an illustration of an example robotic surgical system.

FIG. 8 is an illustration of an example robotic surgical system. In some implementations, one or more surgeons, surgical assistants, surgical technologists and/or other technicians, perform an operation on a patient using a robotic-assisted surgical system. In the operating room the surgeon may be guided by the robotic system to accurately execute an operation. The robotic surgical system may be transported in and out of an operating room using a mobile cart (not shown). Accordingly, the robotic surgical system, including the mobile cart, must be sterilized when used in the operating room. The system may be sterilized by applying a sterile drape 820 to a portion of the system, including the robotic arm 802 and/or the mobile cart. The sterile drape 820 may consist of a single drape or several pieces, such as a sterile cover for covering the robotic arm 802 and a sterile drape for covering the mobile cart.

In some implementations, the sterile drape 820 is attached (e.g., glued or welded) to a sterile adapter 822. The sterile adapter 822 may be attached (e.g., clipped) to a tool holder body 824 on the robotic arm 802. The sterile adapter 822 ensures the drape 820 is tightly stretched over the tool holder 824 to protect the robotic arm 802 and mobile cart from contaminating the sterile field, and provides a structure that provides for repeatable and rigid positioning of the sterile drape. Tightly stretching the drape 820 between the instrument holder 826 and tool holder 824 and tightening the instrument holder 826 to the robotic arm 802 using, for example, a tightening screw 832, reduces the likelihood of folds in the drape between the told holder and robot interface. Thus, errors between the robot model and the actual situation because of the position of the tool holder relative to the robot interface are minimized. If folds are present, the positioning of the instrument holder 826 relative to the robot interface will be different than anticipated and the robotic surgical system may have difficulty positioning tools held by the tool holder appropriately.

A sterile tool holder 826 may be connected to the robotic arm 802 through the sterile drape 820. In some implementations, the instrument holder 826 includes a base 828, clamp 830, and nut 832. In some implementations, the nut is tightened to pull the clamp 830 closer to the base 828 such that a surgical instrument, such as tool guide 814 is securely held between the base 828 and the clamp 830. The instrument holder 826 be coupled to a navigation marker 816. A sterile handle 804 may be mechanically coupled to the tool guide 814 via a handle 818 of the tool guide. A tightening nut 808 on the sterile handle 804 may be used to tighten the sterile handle to the handle 818 such that the sterile handle 804 is securely attached to the handle 818.

In some implementations, the sterile handle 804 includes an input device 806, such as button 806*a* and button 806*b*, that enables a user to control the position of the end effector 820. Thus, the disclosed technology enables a robotic surgical system to be used in a sterile operating room without having to sterilize each individual component of the system. Only the components outside of the sterile drape (e.g., the optical mark, surgical instruments, and tool holder must be sterilized individually.

The input device 806 may mimic the functionality of the mode selection panel 838. Both the input device 806 and the mode selection panel 838. In some implementations, both of these interfaces are configured to enable a user to place the robotic surgical system in one of a rotation mode, a translation mode, or a combined translation and rotation mode. In some implementations, upon selection of a first button of the two or more buttons, the robotic surgical system is in the rotation mode, upon selection of a second button of the two or more buttons, the robotic surgical system is in the translation mode, and upon selection of both the first and second buttons, the robotic surgical system is in the combined translation and rotation mode.

In some implementations, the sterile adapter 822 may be a disposable (e.g. a single-use product). For example, a new sterile adapter 822 may be used for every surgical procedure. In some implementations, the sterile adapter 822 is a rigid or semi-rigid device. It may be made from a hard plastic, polymer, or a composite material. In some implementations, the sterile adapter 822 secures a drape 820 over a surgical robotic arm 802 to prevent contamination of a sterile field.

The sterile adapter 822 may include a rigid or semi-rigid collar (e.g., ring or a hollow cylindrical structure) configured to mount (e.g., snap-mount) onto an interface 824 of the surgical robotic arm. The sterile adapter 822 may include a rigid or semi-rigid body extending from the collar and shaped to conform to a portion of the surgical robotic arm to tightly secure a flexible drape 820 in place (e.g., with no folds) over the portion of the surgical robotic arm 802 when the drape 820 is attached to the adapter 822.

In some implementations, the sterile adapter 822 is one or more tabs that engage an interface on the robot. The tabs may "click" into the interface to provide easy and secure mounting of the sterile adapter 822, and hence sterile drape 820, on the robot. The sterile drape 820 may be glued or welded to the sterile adapter 822. The adapter 822 ensures that the drape is tightly stretched over the instrument holder 826 and tool holder body 824 to provide repeatable and rigid positioning of the instrument holder 826 relative to the robotic arm 802.

In some implementations, a user applies forces and torques on an instrument guide 814 attached to a force/torque sensor 834. The force/torque sensor 834 may be attached to a flange on the robot arm 802 and measures the forces and torques applied to the tool, such as guide 814. In some implementations, the measurements are transmitted to a force control box. In some implementations, the force control box converts the analog data into digitized data and transmits them to a controller. In some implementations, the measurements from force/torque sensor 834 are sent directly to the controller. The controller processes the forces and torques and computes linear and angular correction of the end-effector 840 position of the robot. The controller sends commands to the motors of the robot to update the position of the end effector 840 to a set point position. The controller may check the current position of the position of the end-effector 840 and stops sending commands to the motors if the set point position is reached. In some implementations, this process is performed continuously. In some implementations, the motors are servo or electric motors that are controlled by a servo control. The force sensor 834 may be connected to the robot with an intermediary analog box which measures forces and torques and transmits them via a network (e.g., Ethernet, CAN, wireless, internet, private LAN, public LAN, etc.).

The force sensor 834 may be attached to system in a variety of configurations. In some implementations, the force sensor 834 is coupled to the robot arm 802 using a sensor-robot interface 836. The tool holder body 824 may be coupled to the robotic arm 802 via the force sensor 834. Using this configuration, the sterile cover 820 may be wrapped around the robot arm 802 and between the tool holder body 824 and the instrument holder 826 via the sterile adapter 828 to ensure sterilization. The force sensor 834 may provide for direct measurement of forces on the tool. The force sensor 834 may be designed to resist flexing. The force sensor 834 may be designed to flex under the stress of certain external forces. The displacement caused when an external force is applied may be calculated based on the force applied to the tool, torque applied to the tool, radial force stiffness, axial torque stiffness, and the diameter of the holder to which the tool is attached. In some implementations, the force sensor 834 is located between the tool holder 826 and robot tool holder body 824.

In some implementations, the sterile drape 820 includes a flexible covering with a sterile outer surface. The covering 820 may be at least partially conformable to a surgical robotic arm 802. The sterile drape 820 may include an embedded connector configured (e.g., positioned on the flexible covering and sized) to permit electrical contact between the electronics for controlling the surgical robotic arm (e.g., an actuator of the robotic arm) and the electronics of a sterile handle 804 of the robotic arm 802 when the sterile handle 804 is separated from the surgical robotic arm 802 by the flexible covering 820. In some implementations, the sterile drape 820 is disposable (e.g., a single-use product). In some implementations, the sterile handle 804 is connected to a handle connector 812 via a cable 810. The handle connector 812 may be plugged into or electrically coupled to the embedded connector of the sterile drape 820. In some implementations, an electrical connector is coupled to the electrical system of the robotic surgical system and may be electrically coupled to the embedded connector of the sterile drape 820 such that the handle connector 812 and the electrical connector are electrically coupled to each other through the sterile drape (e.g., via the embedded connector in the drape).

Figure 9:
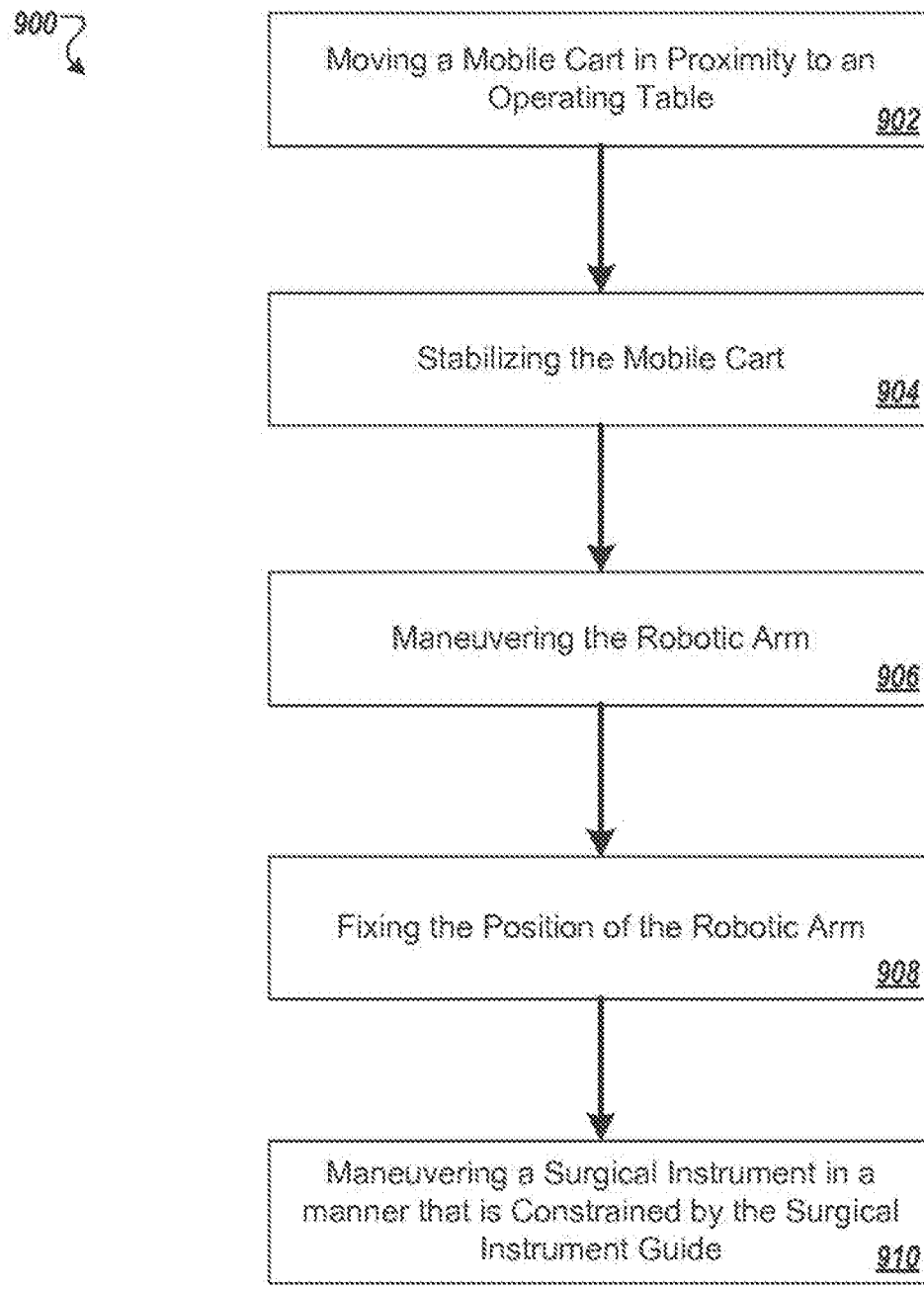
FIG. 9 is a flowchart of an example method of performing surgery with a robotic surgical system.

FIG. 9 is a flowchart of an example method 900 of performing surgery with a robotic surgical system. In some implementations, the method 900 includes moving a mobile cart transporting a robotic surgical system with a robotic arm in proximity to an operating table (902). In some implementations, the robotic arm has an end effector and a sterile handle thereto. In some implementations, the sterile handle includes a tightening sleeve with a hollow tubular structure having a first open end. The structure may define an axis along which a portion of a surgical instrument guide may be inserted into the internal housing. The tightening sleeve may include two or more openings along a length of the tightening sleeve allowing the tightening sleeve to mechanically flex under tension The two or more openings may be slots, holes, perforations, or a combination thereof.

In some implementations, the sterile handle includes a sterile handle housing with a hollow tubular structure having a first open end, said structure defining an axis along which the tightening sleeve may be inserted into the external housing. In some implementations, the sterile handle includes a tightening nut coupled to the sterile handle housing. The tightening nut may include a thread on an interior of the tightening nut and the tightening nut may be configured to engage a thread on exterior of the tightening sleeve and thereby tighten the tightening sleeve such that a diameter of a portion of the tightening sleeve decreases and securely holds a portion of a surgical instrument guide inserted into the internal housing. The portion of the surgical instrument guide inserted into the tightening sleeve may be a portion of the surgical instrument guide handle.

In some implementations, the sterile handle includes an electrical assembly with one or more input devices for commanding the robotic surgical system. The one or more input devices may include two or more buttons configured to enable a user to place the robotic surgical system in one of a rotation mode, a translation mode, or a combined translation and rotation mode. In some implementations, upon selection of a first button of the two or more buttons, the robotic surgical system is in the rotation mode, upon selection of a second button of the two or more buttons, the robotic surgical system is in the translation mode, and upon selection of both the first and second buttons, the robotic surgical system is in the combined translation and rotation mode.

In some implementations, the method 900 includes stabilizing the mobile cart (904). Stabilizing the mobile cart may include extracting one or more rigid legs on the mobile cart such that the mobile cart rests on the one or more rigid legs of the mobile cart. In some implementations, stabilizing the mobile cart includes retracting one or more wheels on the mobile cart such that the mobile cart rests on one or more rigid legs of the mobile cart.

In some implementations, the method 900 includes maneuvering the robotic arm to a desired position to align an axis defined by the surgical instrument at a desired trajectory in relation to a patient situation (906). The desired trajectory may be a desired path of the surgical instrument guide. In some implementations, the method 900 includes, prior to maneuvering the robotic arm to a desired position, obtaining or accessing a CT scan, 3D CT scan, fluoroscopy, 3D fluoroscopy, or natural landmark-based image of the patient situation.

In some implementations, the method 900 includes, after maneuvering the robotic arm to the desired position, fixing the position of the robotic arm (and, therefore, the position of the surgical instrument) (908). In some implementations, the method 900 includes, after fixing the position of the robotic arm, maneuvering the surgical instrument guide in a manner that is constrained by the surgical instrument guide (910). In some implementations, the surgical instrument guide is configured to hold and/or restrict movement of a second surgical instrument therethrough. The surgical instrument may be a drill bit, tap, screw driver, screw-based implant, and awl. In some implementations, the surgical instrument guide is a drill guide and the surgical instrument is a drill bit. Step 910 may include maneuvering the surgical instrument through the surgical instrument guide. For example, step 910 may include maneuvering the drill bit through the drill bit guide. In some implementations, the robotic surgical system is for use in spinal surgery.

In some implementations, the sterile handle includes one or more sensors configured to detect a presence of a surgeon's hand in proximity to the sterile handle. The sensor may include a button or lever that is activated when a user grabs a portion of the sterile handle, thus alerting the system that the hand is present. This may allow the system to detect intentional movements of the robotic arm and/or end effect and unintentional movements which may be avoided or negated by the system (e.g., such that the end effector or arm does not move).

Figure 10A:
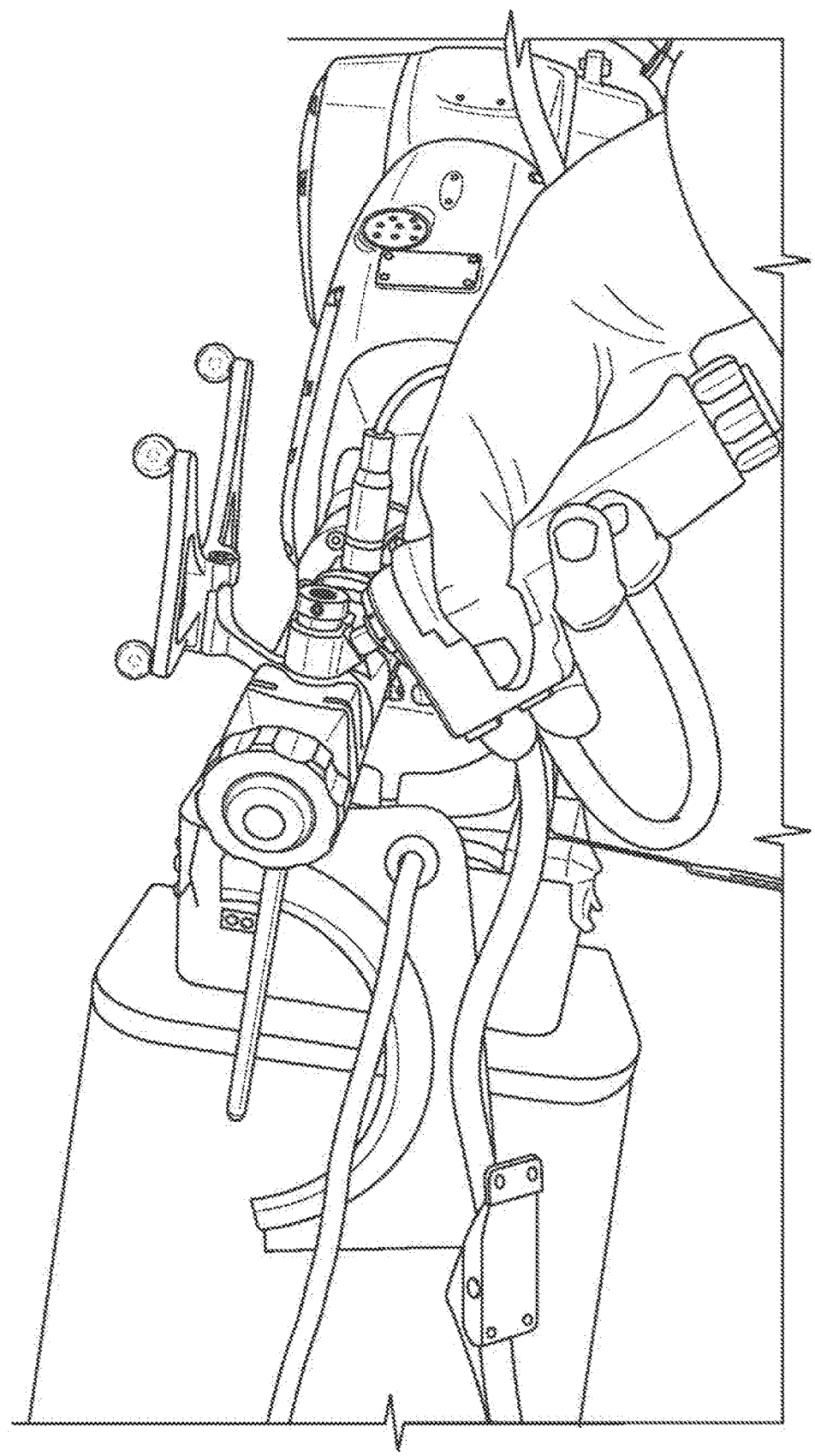
FIGS. 10A-B are illustrations of an example sterile handle rotating along the axis of the sterile handle.
Figure 10B:
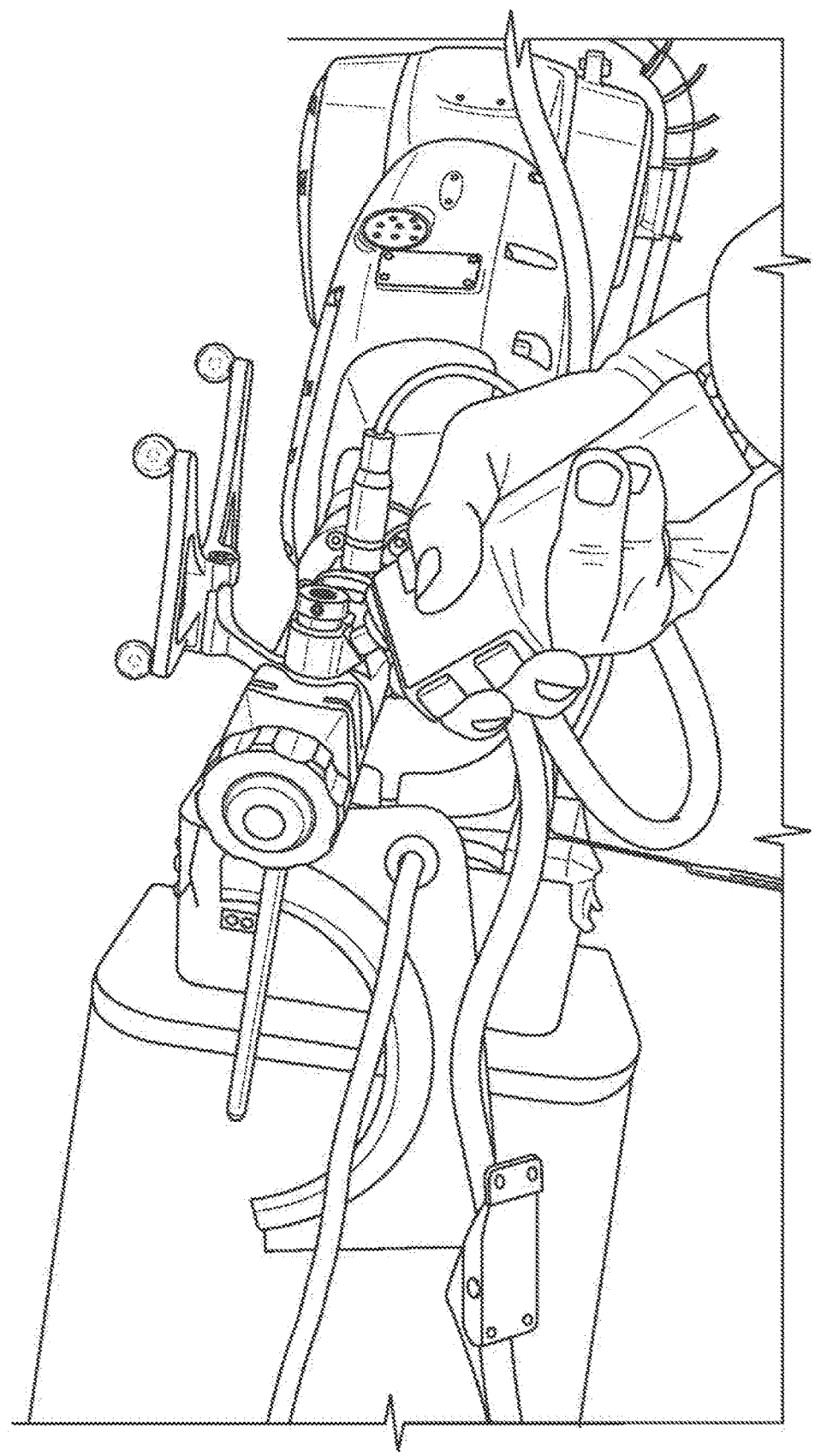
Figure 11A:
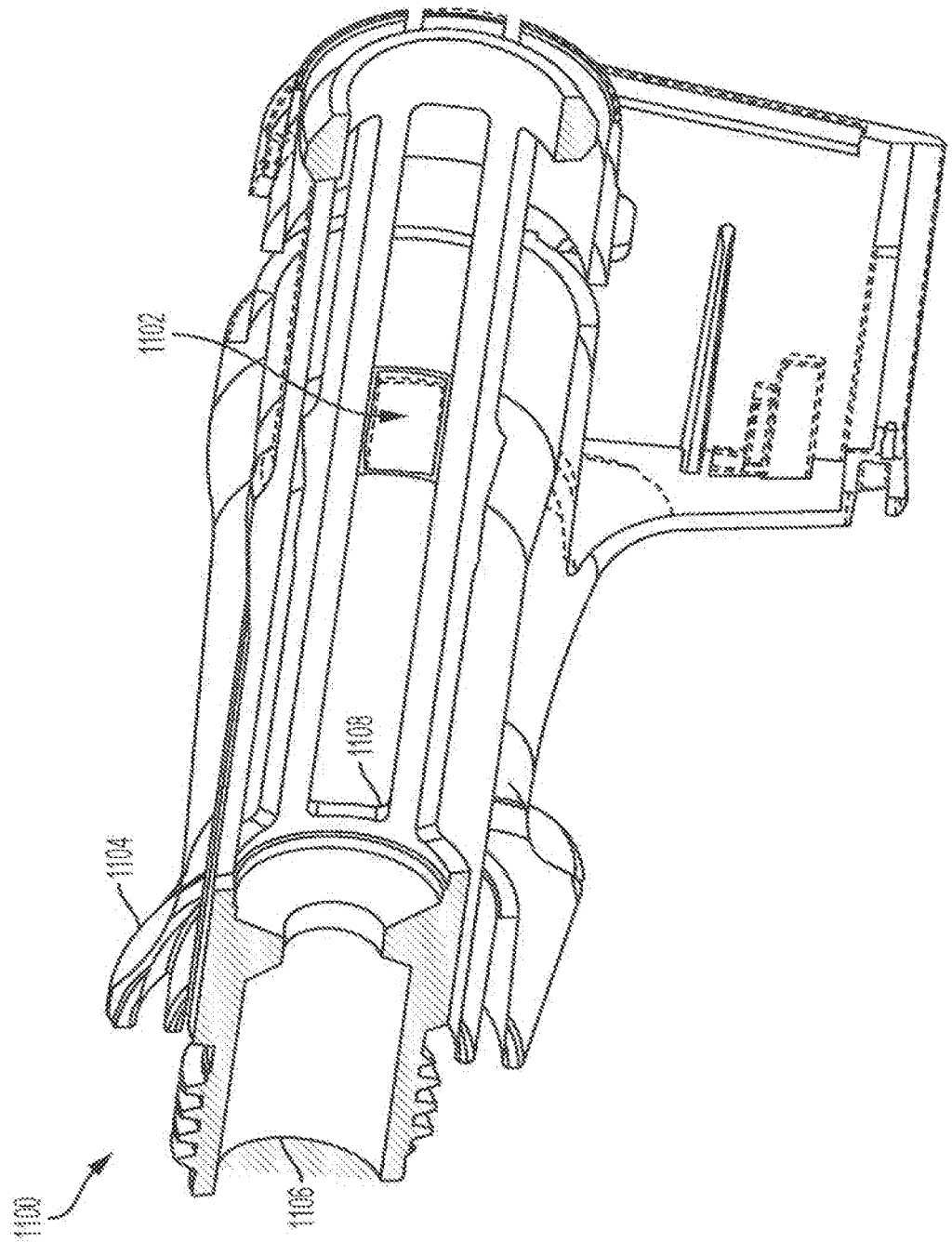
Figure 11B:
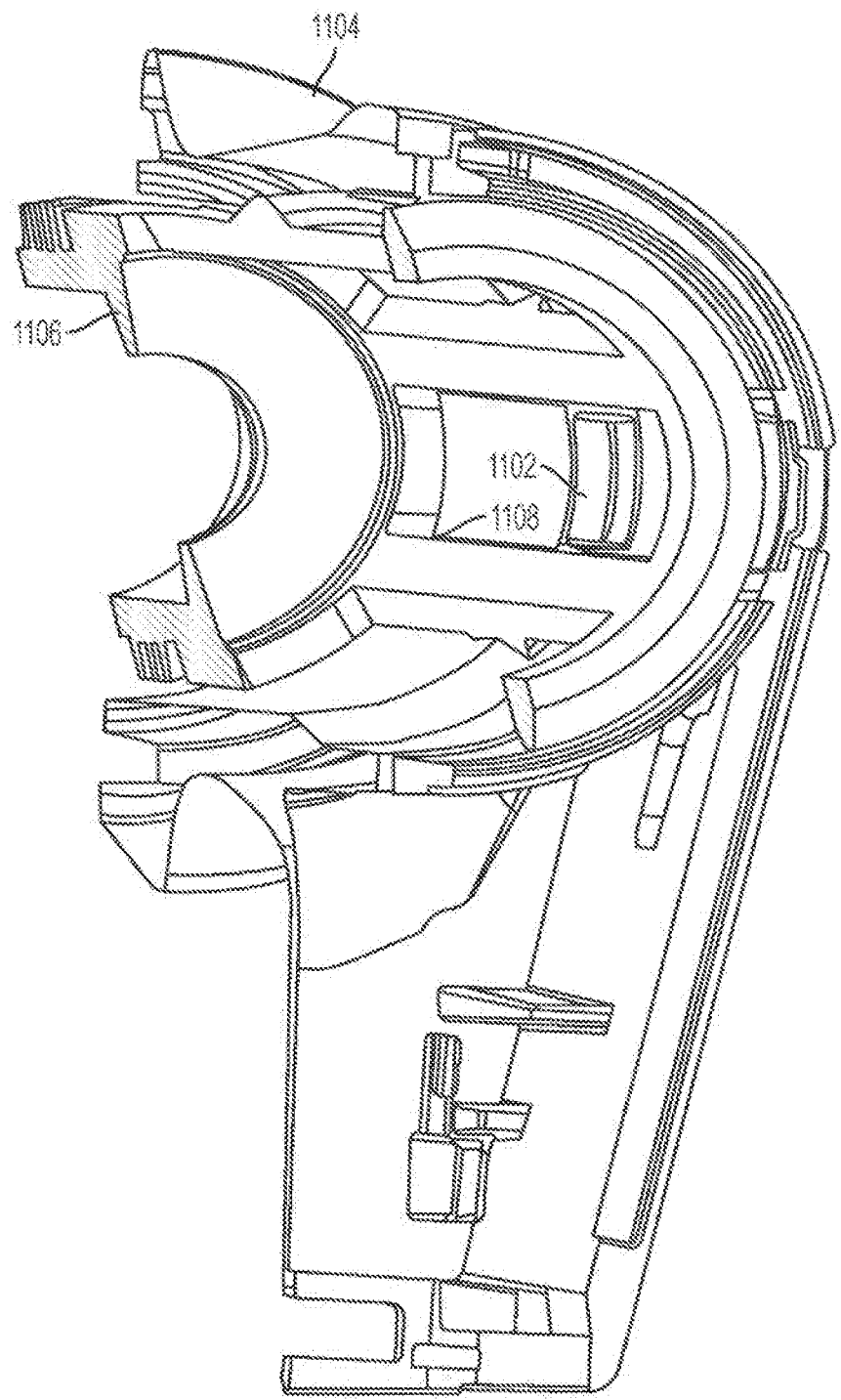

In some implementations, features are added to the sterile handle to prevent rotation of the handle about the axis of the handle when a torque is applied thereto as shown in FIGS. 10A-B. In some implementations, one or more ribs 1102 are added to the external housing 1104 of the sterile handle 1100 (e.g., on the inner surface of the external housing) as shown in FIGS. 11A-C (various cross-sectional views of portions of the sterile handle are shown therein). The one or more ribs 1102 are designed to block rotation along the axis of the sterile handle 1100 by engaging one or more openings 1108, respectively, in the internal housing 1106 of the sterile handle 1100. In the example shown in FIGS. 11A-C, the rib 1102 engages the opening 1108 when the external housing 1104 is slide over the internal housing 1106. In some implementations, several ribs (e.g., two, three, four, five, or six ribs) are integrated in the external housing 1104 (e.g., and at least a corresponding number of openings in the internal housing 1106), thereby decreasing the load on a single rib when a torque is applied to the handle 1100. This allows, for example, a user to apply high torques around the axis of the handle without rotating the handle itself.

In some implementations, the materials used in the design of the handle are such that the friction between the inner and outer housing of the sterile handle as explained above is such that rotation of the axis is prevented (e.g., without using one or more ribs). In some implementations, interface between the inner and outer housings is coated or textured to increase the friction there between, thereby preventing the undesired rotation.

Figure 12A:
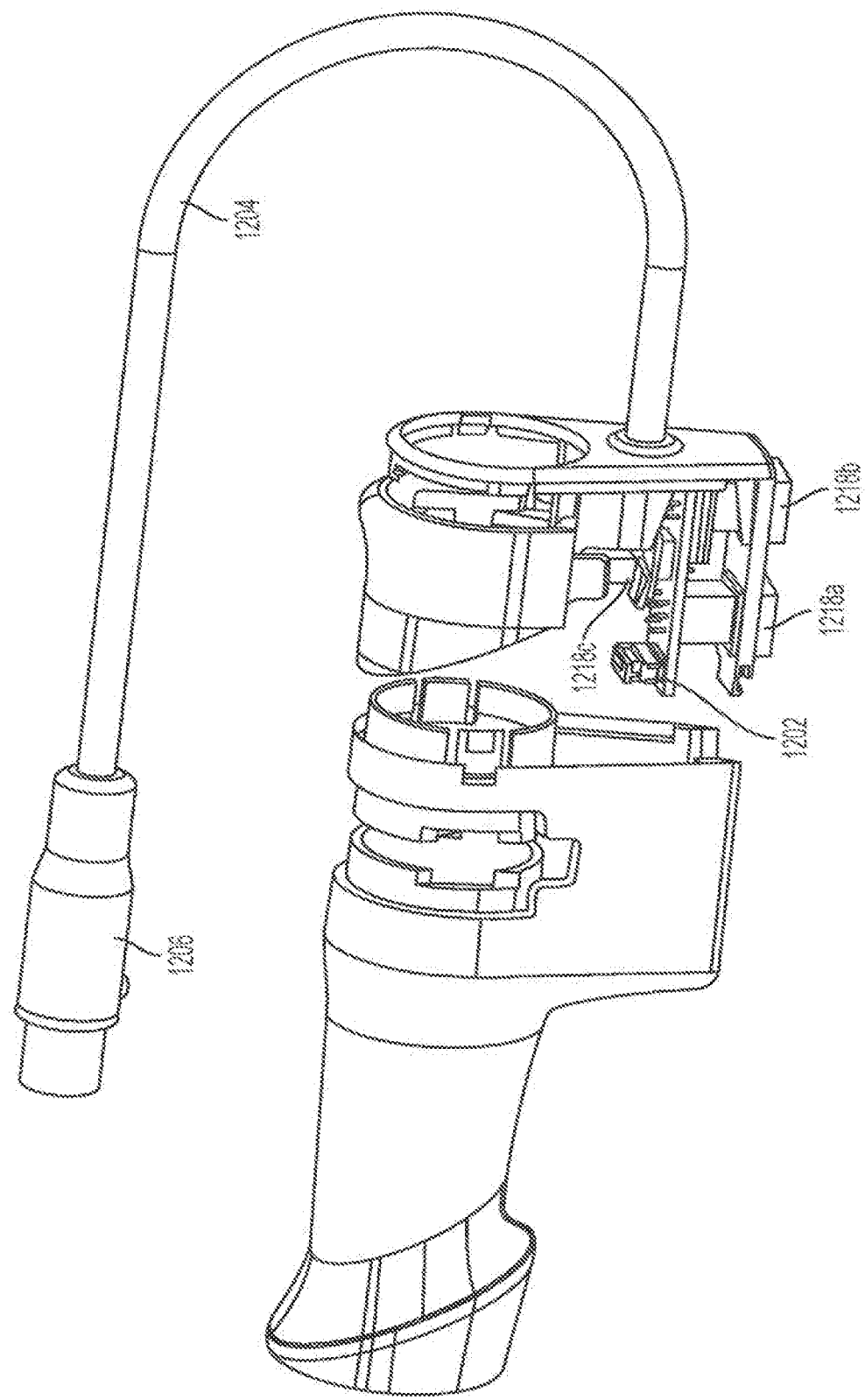
FIG. 12A-C are illustrations of portions of an example sterile handle with an integrated printed circuit board.
Figure 12B:
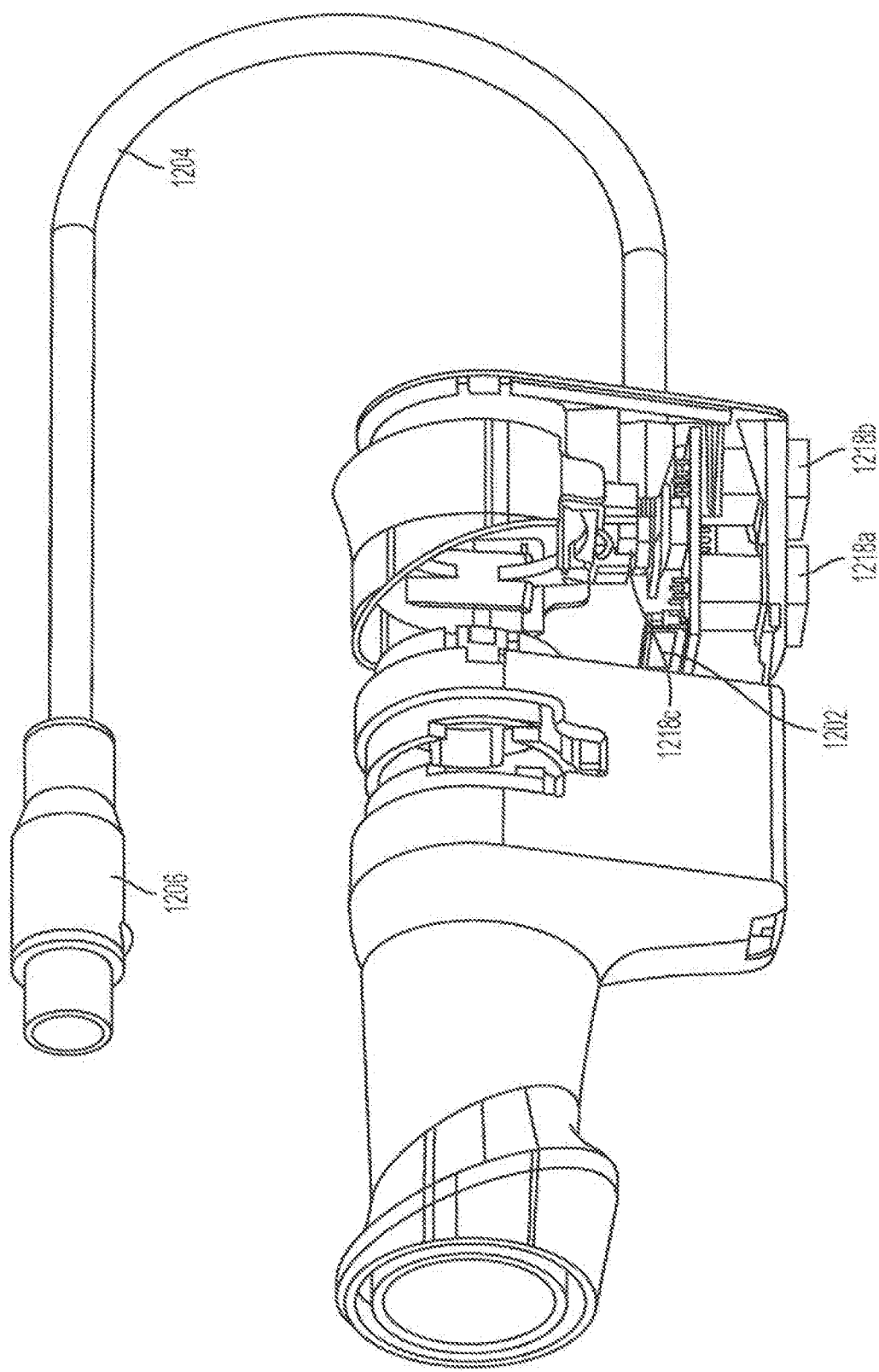
Figure 12C:
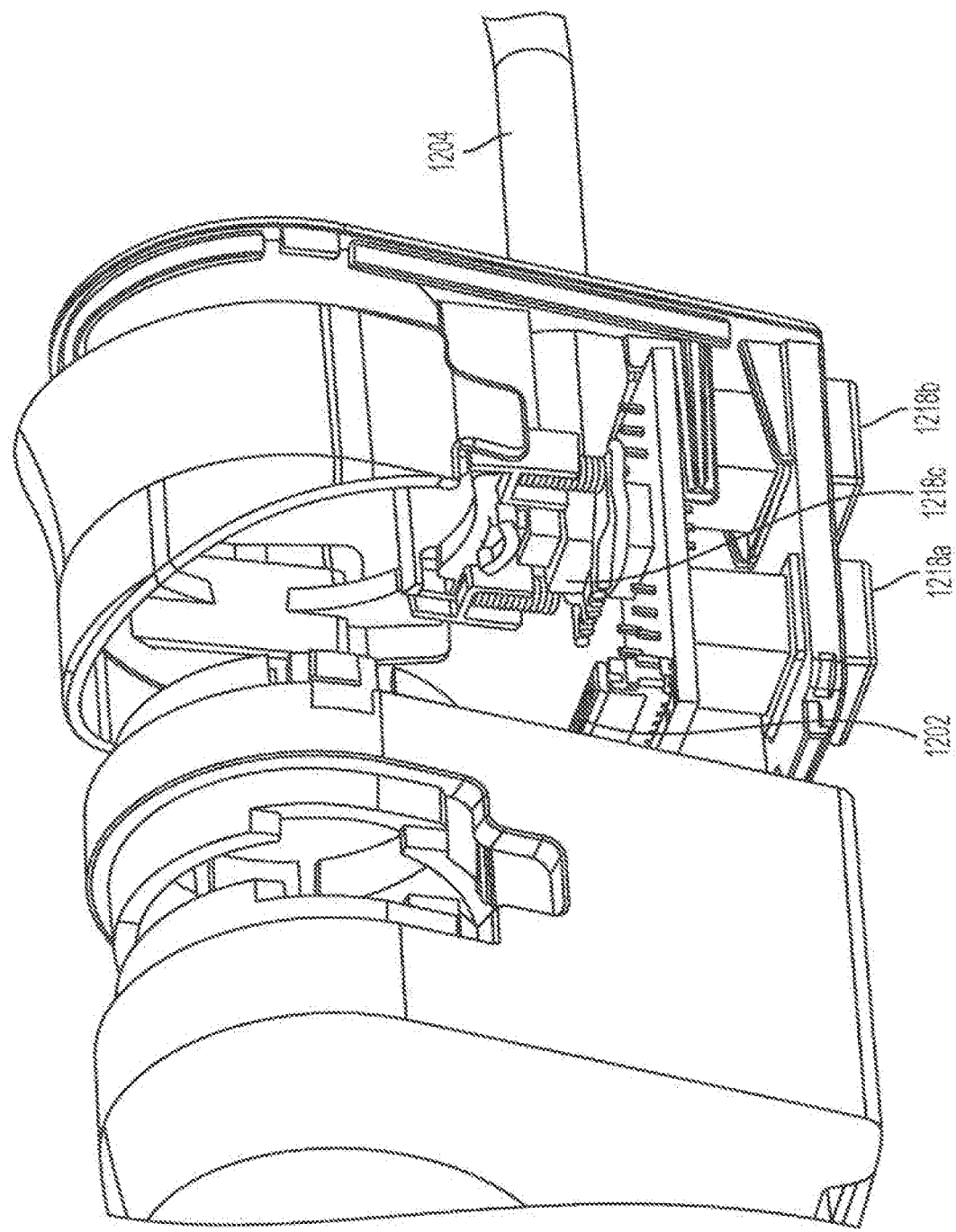

FIGS. 12A-C illustrate portions of an example sterile handle. In certain embodiments, the buttons 1218*a-b* (e.g., buttons 318*a-b* shown in FIG. 3A) are connected to a printed circuit board housed at least partially inside the sterile handle. In some implementations, the printed circuit board is part of the sterile handle housing (i.e., external housing). In some implementations, the printed circuit board is part of the tightening sleeve (i.e., the internal housing of the sterile handle). The printed circuit board (e.g., and the buttons 1218), in some implementations, are preassembled (e.g., prior to assembling the handle). In some implementations, a switch 1218*c* is included such as switch 332 as described in relation to FIG. 3A. In some implementations, the sterile handle (e.g., the input devices on the sterile handle and the movement detection device) are electrically connected to a plug 1206 via a cable 1204. The plug 1206 may be connected to the computer of the robotic surgical system thereby enabling the computer to communicate with the sterile handle and vice versa. In some implementations, a cable connector 1202 is included on the printed circuit board as shown in FIG. 12C.

Figure 13:
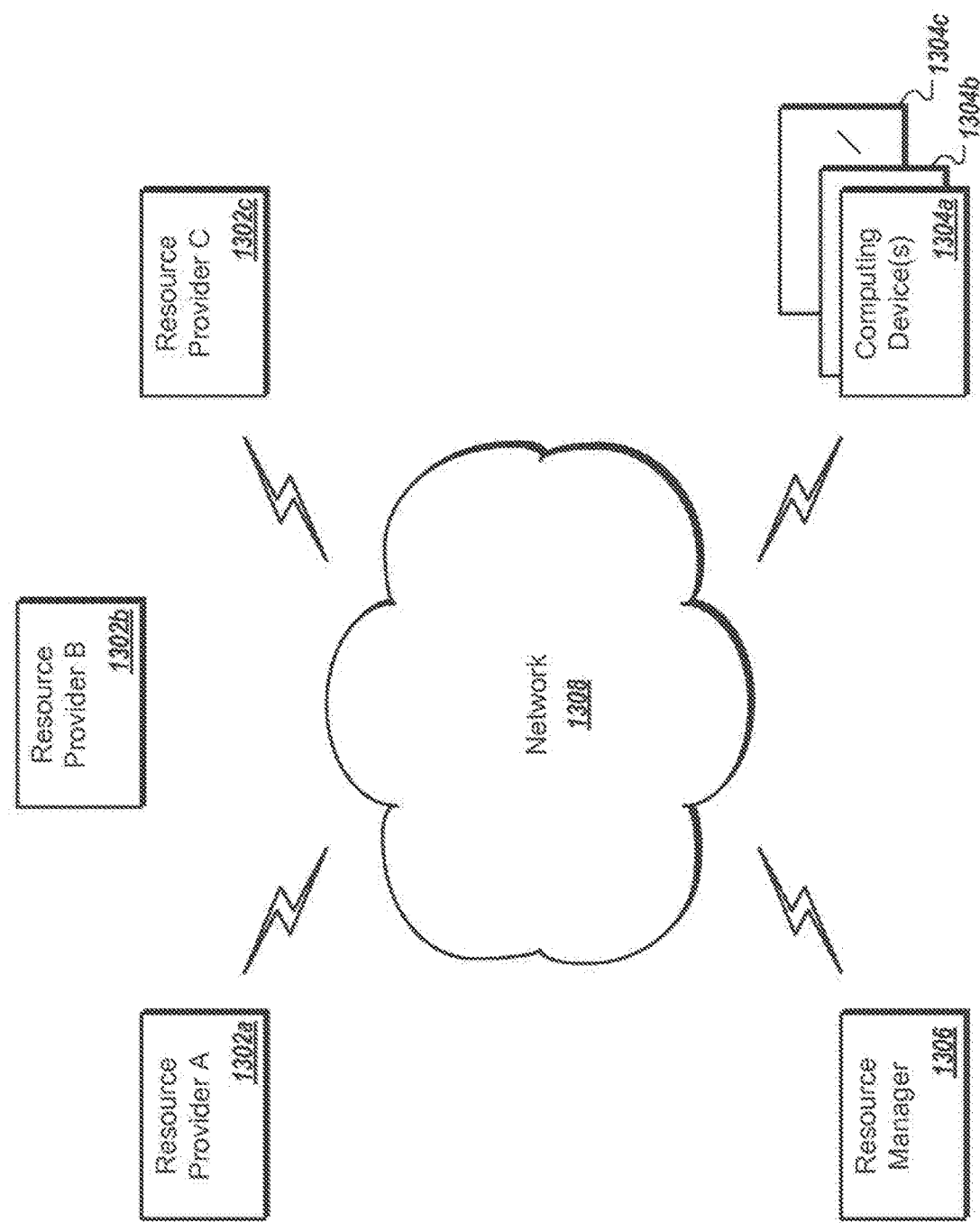
FIG. 13 shows a block diagram of an exemplary cloud computing environment.

As shown in FIG. 13, an implementation of a network environment 1300 for use with a robotic surgical system is shown and described. In brief overview, referring now to FIG. 13, a block diagram of an exemplary cloud computing environment 1300 is shown and described. The cloud computing environment 1300 may include one or more resource providers 1302a, 1302b, 1302c (collectively, 1302). Each resource provider 1302 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 1302 may be connected to any other resource provider 1302 in the cloud computing environment 1300. In some implementations, the resource providers 1302 may be connected over a computer network 1308. Each resource provider 1302 may be connected to one or more computing device 1304a, 1304b, 1304c (collectively, 1304), over the computer network 1308.

The cloud computing environment 1300 may include a resource manager 1306. The resource manager 1306 may be connected to the resource providers 1302 and the computing devices 1304 over the computer network 1308. In some implementations, the resource manager 1306 may facilitate the provision of computing resources by one or more resource providers 1302 to one or more computing devices 1304. The resource manager 1306 may receive a request for a computing resource from a particular computing device 1304. The resource manager 1306 may identify one or more resource providers 1302 capable of providing the computing resource requested by the computing device 1304. The resource manager 1306 may select a resource provider 1302 to provide the computing resource. The resource manager 1306 may facilitate a connection between the resource provider 1302 and a particular computing device 1304. In some implementations, the resource manager 1306 may establish a connection between a particular resource provider 1302 and a particular computing device 1304. In some implementations, the resource manager 1306 may redirect a particular computing device 1304 to a particular resource provider 1302 with the requested computing resource.

Figure 14:
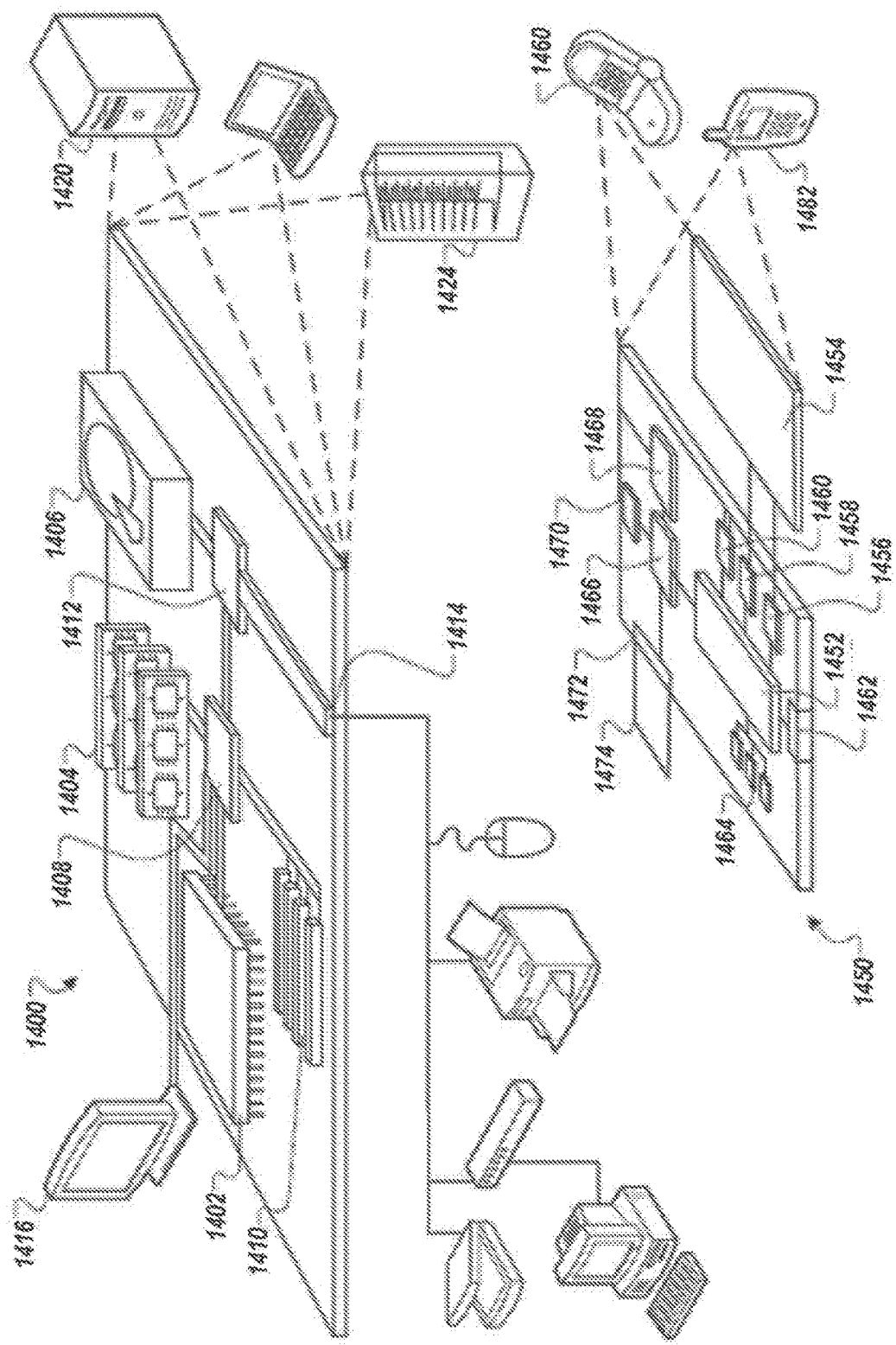
FIG. 14 is a block diagram of a computing device and a mobile computing device.

FIG. 14 shows an example of a computing device 1400 and a mobile computing device 1450 that can be used to implement the techniques described in this disclosure. The computing device 1400 is intended to represent various forms of digital computers, such as laptops, desktops, workstations, personal digital assistants, servers, blade servers, mainframes, and other appropriate computers. The mobile computing device 1450 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 1400 includes a processor 1402, a memory 1404, a storage device 1406, a high-speed interface 1408 connecting to the memory 1404 and multiple high-speed expansion ports 1410, and a low-speed interface 1412 connecting to a low-speed expansion port 1414 and the storage device 1406. Each of the processor 1402, the memory 1404, the storage device 1406, the high-speed interface 1408, the high-speed expansion ports 1410, and the low-speed interface 1412, are interconnected using various busses, and may be mounted on a common motherboard or in other manners as appropriate. The processor 1402 can process instructions for execution within the computing device 1400, including instructions stored in the memory 1404 or on the storage device 1406 to display graphical information for a GUI on an external input/output device, such as a display 1416 coupled to the high-speed interface 1408. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory 1404 stores information within the computing device 1400. In some implementations, the memory 1404 is a volatile memory unit or units. In some implementations, the memory 1404 is a non-volatile memory unit or units. The memory 1404 may also be another form of computer-readable medium, such as a magnetic or optical disk.

The storage device 1406 is capable of providing mass storage for the computing device 1400. In some implementations, the storage device 1406 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 1402), perform one or more methods, such as those described above. The instructions can also be stored by one or more storage devices such as computer- or machine-readable mediums (for example, the memory 1404, the storage device 1406, or memory on the processor 1402).

The high-speed interface 1408 manages bandwidth-intensive operations for the computing device 1400, while the low-speed interface 1412 manages lower bandwidth-intensive operations. Such allocation of functions is an example only. In some implementations, the high-speed interface 1408 is coupled to the memory 1404, the display 1416 (e.g., through a graphics processor or accelerator), and to the high-speed expansion ports 1410, which may accept various expansion cards (not shown). In the implementation, the low-speed interface 1412 is coupled to the storage device 1406 and the low-speed expansion port 1414. The low-speed expansion port 1414, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 1400 may be implemented in a number of different forms, as shown in the figure. For example, it may be implemented as a standard server 1420, or multiple times in a group of such servers. In addition, it may be implemented in a personal computer such as a laptop computer 1422. It may also be implemented as part of a rack server system 1424. Alternatively, components from the computing device 1400 may be combined with other components in a mobile device (not shown), such as a mobile computing device 1450. Each of such devices may contain one or more of the computing device 1400 and the mobile computing device 1450, and an entire system may be made up of multiple computing devices communicating with each other.

The mobile computing device 1450 includes a processor 1452, a memory 1464, an input/output device such as a display 1454, a communication interface 1466, and a transceiver 1468, among other components. The mobile computing device 1450 may also be provided with a storage device, such as a micro-drive or other device, to provide additional storage. Each of the processor 1452, the memory 1464, the display 1454, the communication interface 1466, and the transceiver 1468, are interconnected using various buses, and several of the components may be mounted on a common motherboard or in other manners as appropriate.

The processor 1452 can execute instructions within the mobile computing device 1450, including instructions stored in the memory 1464. The processor 1452 may be implemented as a chipset of chips that include separate and multiple analog and digital processors. The processor 1452 may provide, for example, for coordination of the other components of the mobile computing device 1450, such as control of user interfaces, applications run by the mobile computing device 1450, and wireless communication by the mobile computing device 1450.

The processor 1452 may communicate with a user through a control interface 1458 and a display interface 1456 coupled to the display 1454. The display 1454 may be, for example, a TFT (Thin-Film-Transistor Liquid Crystal Display) display or an OLED (Organic Light Emitting Diode) display, or other appropriate display technology. The display interface 1456 may comprise appropriate circuitry for driving the display 1454 to present graphical and other information to a user. The control interface 1458 may receive commands from a user and convert them for submission to the processor 1452. In addition, an external interface 1462 may provide communication with the processor 1452, so as to enable near area communication of the mobile computing device 1450 with other devices. The external interface 1462 may provide, for example, for wired communication in some implementations, or for wireless communication in other implementations, and multiple interfaces may also be used.

The memory 1464 stores information within the mobile computing device 1450. The memory 1464 can be implemented as one or more of a computer-readable medium or media, a volatile memory unit or units, or a non-volatile memory unit or units. An expansion memory 1474 may also be provided and connected to the mobile computing device 1450 through an expansion interface 1472, which may include, for example, a SIMM (Single In Line Memory Module) card interface. The expansion memory 1474 may provide extra storage space for the mobile computing device 1450, or may also store applications or other information for the mobile computing device 1450. Specifically, the expansion memory 1474 may include instructions to carry out or supplement the processes described above, and may include secure information also. Thus, for example, the expansion memory 1474 may be provided as a security module for the mobile computing device 1450, and may be programmed with instructions that permit secure use of the mobile computing device 1450. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier and, when executed by one or more processing devices (for example, processor 1452), perform one or more methods, such as those described above. The instructions can also be stored by one or more storage devices, such as one or more computer- or machine-readable mediums (for example, the memory 1464, the expansion memory 1474, or memory on the processor 1452). In some implementations, the instructions can be received in a propagated signal, for example, over the transceiver 1468 or the external interface 1462.

The mobile computing device 1450 may communicate wirelessly through the communication interface 1466, which may include digital signal processing circuitry where necessary. The communication interface 1466 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 1468 using a radio-frequency. In addition, short-range communication may occur, such as using a Bluetooth®, Wi-Fi™, or other such transceiver (not shown). In addition, a GPS (Global Positioning System) receiver module 1470 may provide additional navigation- and location-related wireless data to the mobile computing device 1450, which may be used as appropriate by applications running on the mobile computing device 1450.

The mobile computing device 1450 may also communicate audibly using an audio codec 1460, which may receive spoken information from a user and convert it to usable digital information. The audio codec 1460 may likewise generate audible sound for a user, such as through a speaker, e.g., in a handset of the mobile computing device 1450. Such sound may include sound from voice telephone calls, may include recorded sound (e.g., voice messages, music files, etc.) and may also include sound generated by applications operating on the mobile computing device 1450.

The mobile computing device 1450 may be implemented in a number of different forms, as shown in the figure. For example, it may be implemented as a cellular telephone 1480. It may also be implemented as part of a smart-phone 1482, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In view of the structure, functions and apparatus of the systems and methods described here, in some implementations, a system and method for performing surgery with a robotic surgical system are provided. Having described certain implementations of methods and apparatus for supporting a robotic surgical system, it will now become apparent to one of skill in the art that other implementations incorporating the concepts of the disclosure may be used. Therefore, the disclosure should not be limited to certain implementations, but rather should be limited only by the spirit and scope of the following claims.

Throughout the description, where apparatus and systems are described as having, including, or comprising specific components, or where processes and methods are described as having, including, or comprising specific steps, it is contemplated that, additionally, there are apparatus, and systems of the disclosed technology that consist essentially of, or consist of, the recited components, and that there are processes and methods according to the disclosed technology that consist essentially of, or consist of, the recited processing steps.

It should be understood that the order of steps or order for performing certain action is immaterial so long as the disclosed technology remains operable. Moreover, two or more steps or actions may be conducted simultaneously.

What is claimed is:

1. A method of performing surgery with a robotic surgical system, the method comprising:
   moving a mobile cart transporting a robotic surgical system comprising a robotic arm in proximity to an operating table, wherein the robotic arm has an end effector comprising a surgical instrument guide for guiding a surgical instrument, the surgical instrument guide having an internal handle and a sterile handle, wherein the sterile handle comprises:
   a tightening sleeve comprising a hollow tubular structure having a first open end, said structure defining an axis along which the internal handle of the surgical instrument guide may be inserted, the tightening sleeve comprising two or more openings along a length of the tightening sleeve allowing the tightening sleeve to mechanically flex under tension, wherein no part of the surgical instrument is received in the tightening sleeve,
   a sterile handle housing comprising a hollow tubular structure having a first open end, said structure of the sterile handle housing defining an axis along which the tightening sleeve may be inserted,
   a tightening nut coupled to the sterile handle housing and comprising a thread on an interior of the tightening nut, wherein the tightening nut is configured to engage a thread on exterior of the tightening sleeve and thereby tighten the tightening sleeve such that a diameter of a portion of the tightening sleeve decreases and securely holds a portion of the internal handle of the surgical instrument guide, and
   an electrical assembly comprising one or more input devices for commanding the robotic surgical system;
   stabilizing the mobile cart;
   maneuvering the robotic arm to a desired position to align an axis defined by the surgical instrument guide at a desired trajectory in relation to a patient situation;
   fixing the position of the robotic arm; and
   maneuvering a surgical instrument in a manner that is constrained by the surgical instrument guide.

2. The method of claim 1, wherein the surgical instrument guide is configured to at least one of hold and restrict movement of a second surgical instrument therethrough.

3. The method of claim 2, wherein the surgical instrument is a drill bit.

4. The method of claim 3, wherein the surgical instrument guide is a drill bit guide.

5. The method of claim 4, further comprising: maneuvering the drill bit through the drill bit guide.

6. The method of claim 1, further comprising: maneuvering the surgical instrument through the surgical instrument guide.

7. The method of claim 1, wherein the robotic surgical system is for use in spinal surgery.

8. The method of claim 1, wherein the one or more input devices comprises two or more buttons configured to enable a user to active one or more of the two or more buttons to place the robotic surgical system in one of a rotation mode, a translation mode, or course positioning mode that allows translation and rotation movements.

9. The method of claim 8, wherein, upon selection of a first button of the two or more buttons, the robotic surgical system is in the rotation mode, upon selection of a second button of the two or more buttons, the robotic surgical system is in the translation mode, and upon selection of both the first and second buttons, the robotic surgical system is in the combined translation and rotation mode.

10. The method of claim 1, wherein the surgical instrument guide includes a guide tube having an axis which is disposed at an angle to the axis of the internal handle.

11. The method of claim 1, wherein the sterile handle comprises one or more sensors configured to detect a presence of a surgeon's hand in proximity to the sterile handle.

12. The method of claim 1, wherein the sterile handle is configured to be attached directly or indirectly to an end-effector of the robotic surgical system.

13. The method of claim 1, wherein the robotic surgical system is configured to allow robotically-assisted or unassisted positioning and/or movement of the sterile handle by a user with at least six degrees of freedom, wherein the six degrees of freedom are three degrees of translations and three degrees of rotations.

14. The method of claim 1, wherein the sterile handle is at least one of completely or partially disposable.

15. The method of claim 1, wherein the surgical instrument guide is configured to be used to guide a screw implant and a tissue protector.

16. The method of claim 1, wherein the sterile handle is removably attached to the robotic arm.

17. The method of claim 16, wherein the axis can be aligned with the desired trajectory in relation to the patient situation via the sterile handle.

18. The method of claim 17, wherein stabilizing the mobile cart comprises extracting one or more rigid legs on the mobile cart such that the mobile cart rests on the one or more rigid legs of the mobile cart.

19. The method of claim 18, wherein stabilizing the mobile cart comprises retracting one or more wheels on the mobile cart such that the mobile cart rests on one or more rigid legs of the mobile cart.

20. A method of performing surgery with a robotic surgical system, the method comprising:

moving a mobile cart transporting a robotic surgical system comprising a robotic arm, wherein the robotic arm has an end effector comprising a surgical instrument guide for guiding a surgical instrument, the surgical instrument guide having an internal handle and a sterile handle, wherein the sterile handle comprises:

a tightening sleeve comprising a hollow tubular structure having a first open end, said structure defining an axis along which the internal handle of the surgical instrument guide may be inserted, the tightening sleeve configured to mechanically flex under tension, wherein no part of the surgical instrument is received in the tightening sleeve, a sterile handle housing comprising a hollow tubular structure having a first open end, said structure of the sterile handle housing defining an axis along which the tightening sleeve may be inserted, a tightening nut coupled to the sterile handle housing and comprising a thread on an interior of the tightening nut, wherein the tightening nut is configured to engage a thread on exterior of the tightening sleeve and thereby tighten the tightening sleeve such that a diameter of a portion of the tightening sleeve decreases and securely holds a portion of the internal handle of the surgical instrument guide, and an electrical assembly comprising one or more input devices for commanding the robotic surgical system;

stabilizing the mobile cart;

maneuvering the robotic arm to a desired position to align an axis defined by the surgical instrument guide at a desired trajectory in relation to a patient situation.

* * * * *